US012680081B2

(12) United States Patent
Park et al.

(10) Patent No.: US 12,680,081 B2
(45) Date of Patent: Jul. 14, 2026

(54) HUMAN INDUCED PLURIPOTENT STEM CELL LINE TRANSFORMED WITH FLUORESCENT PROTEIN-LABELED CYTOCHROME P450 AND AHR MODULATOR SCREENING METHOD USING SAME

(71) Applicant: KOREA RESEARCH INSTITUTE OF CHEMICAL TECHNOLOGY, Daejeon (KR)

(72) Inventors: Han-Jin Park, Daejeon (KR); Ji-Woo Kim, Daejeon (KR); Ilkyun Im, Daejeon (KR); Hyemin Kim, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 742 days.

(21) Appl. No.: 18/010,932

(22) PCT Filed: Mar. 19, 2021

(86) PCT No.: PCT/KR2021/003425
§ 371 (c)(1),
(2) Date: Dec. 16, 2022

(87) PCT Pub. No.: WO2021/256668
PCT Pub. Date: Dec. 23, 2021

(65) Prior Publication Data
US 2023/0235294 A1 Jul. 27, 2023

(30) Foreign Application Priority Data
Jun. 19, 2020 (KR) ........................ 10-2020-0075214

(51) Int. Cl.
*C12N 5/074* (2010.01)

(52) U.S. Cl.
CPC ........ *C12N 5/0696* (2013.01); *C12N 2503/02* (2013.01); *C12N 2510/00* (2013.01)

(58) Field of Classification Search
None
See application file for complete search history.

(56) References Cited

U.S. PATENT DOCUMENTS

2020/0080112 A1* 3/2020 Zhang ...................... C12N 9/22

FOREIGN PATENT DOCUMENTS

KR 10-2019-0092898 A 8/2019

OTHER PUBLICATIONS

Lu et al. Selection of alkaline phosphatase-positive induced pluripotent stem cells from human amniotic fluid-derived cells by feeder-free system. Exp Cell Res. Aug. 1, 2011;317(13):1895-903. Epub May 26, 2011. (Year: 2011).*
Kim et al. Live-cell screening platform using human-induced pluripotent stem cells expressing fluorescence-tagged cytochrome P450 1A1. FASEB J. Jul. 2020;34(7):9141-9155. Epub May 18, 2020. (Year: 2020).*
National Research Council (US) and Institute of Medicine (US) Committee on the Biological and Biomedical Applications of Stem Cell Research. Stem Cells and the Future of Regenerative Medicine. Washington (DC): National Academies Press (US); 2002. Chapter Three, Embryonic Stem Cells. (Year: 2002).*
Takahashi et al. Induction of Pluripotent Stem Cells from Adult Human Fibroblasts by Defined Factors. Cell. Nov. 30, 2007;131(5):861-72. (Year: 2007).*
Angelos et al., "Aryl hydrocarbon receptor inhibition promotes hematolymphoid development from human pluripotent stem cells", Blood, Jun. 29, 2017, vol. 129, No. 26, pp. 3428-3439.
Barouki et al., "The aryl hydrocarbon receptor, more than a xenobiotic-interacting protein", FEBS Letters, vol. 581, 2007, pp. 3608-3615.
Grskovic et al., "Induced pluripotent stem cells—opportunities for disease modelling and drug discovery", Nat Rev Drug Discov, Dec. 2011, vol. 10, No. 12, pp. 915-929.
International Search Report and Written Opinion received for PCT Patent Application No. PCT/KR2021/003425, mailed on Sep. 28, 2021, 18 pages (4 pages of English Translation and 14 pages of Original Document).
Kim et al., "Live-cell screening platform using human-induced pluripotent stem cells expressing fluorescence-tagged cytochrome P450 1A1", FASEB J, Apr. 21, 2020 , vol. 34, No. 7, pp. 1-15.
Kim, H. et al., "Generation of a PXR reporter human induced pluripotent stem cell line (PXR-mCherry hiPSC) using the CRISPR/Cas9 system", Stem Cell Research, 2018, vol. 26, pp. 72-75.
Kolluri et al., "Role of the Aryl Hydrocarbon Receptor in Carcinogenesis and Potential as an Anti-Cancer Drug Target", Arch Toxicol. Jul. 2017, vol. 91, No. 7, pp. 2497-2513.
Nagy S.R. et al., Development of a Green Fluorescent Protein-Based Cell Bioassay for the Rapid and Inexpensive Detection and Characterization of Ah Receptor Agonists, Toxicological Sciences, vol. 65, Issue 2, Feb. 2002, pp. 200-210.
Smith et al., "Genome Editing of the CYP1A1 Locus in iPSCs as a Platform to Map AHR Expression throughout Human Development", Stem Cells International, 2016, vol. 2016, 12 Pages.

(Continued)

*Primary Examiner* — Valarie E Bertoglio
*Assistant Examiner* — Briana N Ebbinghaus
(74) *Attorney, Agent, or Firm* — Fredrikson & Byron, P.A.

(57) ABSTRACT

The present invention relates to a human induced pluripotent stem cell line transformed with fluorescent protein-tagged CYP1A1 and an AHR modulator screening method using the same. Specifically, a human-induced pluripotent stem cell line (hiPSC line) in which a gene was edited to express a cytochrome P450 1A1 (CYP1A1) protein in a state of fusion with a fluorescent protein without inhibiting its unique function was prepared, and it was confirmed that an AHR modulator could be screened by screening cells in a living state using the cell line-derived liver cells better than in the case of using existing human primary hepatocytes (hPH) or HepG2 cells. Therefore, the CYP1A1-mCherry hiPSC cell line of the present invention can be effectively used for screening AHR modulating compounds.

11 Claims, 43 Drawing Sheets
(10 of 43 Drawing Sheet(s) Filed in Color)

Specification includes a Sequence Listing.

(56)            References Cited

OTHER PUBLICATIONS

Zwaka et al., "Homologous recombination in human embryonic stem cells", Nature Biotechnology, Mar. 2003, vol. 21. No. 3, pp. 319-321.

* cited by examiner

FIG. 1b

*E4-E5 intron*

GTAGGTAGTGGCTCCCTTCAAAGGGGTCAGTGCCAGGGGTCTGGCCAGGTCTAGGCAGCCCCTGCATCCATCTTGTCC guide#4          PAM PAM          guide#5

*E6-E7 intron*

ATATGATTAATACAATCATTGCATTGATCCTCCTGTCCATGGGCTGCTTGCCTGTCCTCTATCCTTTGGGGCTGGAGC guide#1          PAM Indel (%) : 52.4%                    52.1%    62%

FIG. 1d

3' junction (F1 & R1)
NC   KI        1-2  1-7  1-8  1-9  1-11 4-1 4-10 4-12  4-13 5-2  5-4 5-5

5'-3' junction (F2 & R1)
NC   KI        1-2  1-7  1-8  1-9  1-11 4-1 4-10 4-12  4-13 5-2  5-4 5-5

FIG. 1e

Ectoderm    Mesoderm    Endoderm

Nestin DAPI    α-SMA DAPI    AFP DAPI

TUJ1 DAPI    DESMIN DAPI    SOX17 DAPI

LDL-uptake

BaP

TCDD

KEGG-pathway: hsa00980
Metabolism of xenobiotics by cytochrome P450

HUMAN INDUCED PLURIPOTENT STEM CELL LINE TRANSFORMED WITH FLUORESCENT PROTEIN-LABELED CYTOCHROME P450 AND AHR MODULATOR SCREENING METHOD USING SAME

CROSS REFERENCE TO RELATED APPLICATIONS

This patent application is a nationalization of and claims priority to PCT Application No. PCT/KR2021/003425 filed on Mar. 19, 2021, which claims priority under 35 U.S.C. § 119 from Korean Patent Application 10-2020-0075214 filed on Jun. 19, 2020. Each of the aforementioned applications are incorporated by reference herein in their entirety.

BACKGROUND OF THE INVENTION

1. Field of the Invention

The present invention relates to a fluorescent protein-tagged cytochrome P450 transformed human induced pluripotent stem cells and screening method of AHR regulator using the same.

2. Description of the Related Art

Human induced pluripotent stem cell (hiPSC) technology offers many possibilities in the fields of novel drug discovery and regenerative medicine. The advantages of hiPSC with properties such as self-renewal and pluripotency have enabled the promotion of hiPSC-based clinical application and disease modeling. Recently, advances and improvements in stem cell differentiation and genome editing techniques have demonstrated the potential for use of hiPSC-derived cells not only in disease modeling but also in drug screening for efficacy and potential toxicity (Grskovic, M., Javaherian, A., Strulovici, B., and Daley, G. Q. (2011) Induced pluripotent stem cells—opportunities for disease modeling and drug discovery. Nat Rev Drug Discov 10, 915-929).

Genetically modified human pluripotent stem cell (hPSC) lines, which refer to both hESC and hiPSC lines, include targeted reporters or selectable markers. These cell lines allow to reveal the underlying mechanisms involved in cell lineage determination, optimize differentiation protocols to derive desired cell types, and isolate pure cell populations for basic and clinical applications. Several initial approaches employing conventional gene targeting techniques based on homologous recombination (HR) pathway have been successfully used in hPSCs (Zwaka, T. P., and Thomson, J. A. (2003) Homologous recombination in human embryonic stem cells. Nat Biotechnol 21, 319-321). However, the low targeting efficiency (~1%) of HR is a limitation that prevents widespread application of genetic modifications in hPSCs.

This limitation can be overcome via CRISPR-Cas9 system. Targeting of the gene locus in the CRISPR-Cas9 system is mediated by a guide RNA consisting of 20 bases that recognize the target DNA sequence and a Cas9 protein involved in DNA cleavage. The CRISPR-Cas9 system facilitates homologous recombination (HR) and improves targeting efficiency by enabling targeted introduction of DNA double-strand breaks (DSBs) at the location of interest. Due to its high targeting efficiency and simplicity, the CRISPR-Cas9 system has been able to generate target reporter lines rapidly (>8%) in hPSCs.

On the other hand, an aryl hydrocarbon receptor (AHR) is a ligand-activated transcription factor that not only functions as a sensor for extracellular signals and environmental ligands, but also mediates numerous toxicological consequences associated with various environmental xenobiotics. In the binding of ligands such as 2,3,7,8-tetrachlorodibenzo-p-dioxin (TCDD), an activated AHR moves to the nucleus and forms a heterodimer with an AHR nuclear translocator (ARNT), resulting in transcriptional induction of several cytochrome P450 enzymes that play an important role in the activation of carcinogens. The importance of AHR activation in biochemical reactions has attracted attention during the past 30 years regarding the mediation of toxic effects by selected xenobiotics and the initiation of malignant tumors. However, recent studies have reported an important regulatory role for AHR in physiological and developmental processes as well as cancer progression in the absence of environmental xenobiotics (Barouki, R., Coumoul, X., and Fernandez-Salguero, P. M. (2007) The aryl hydrocarbon receptor, more than a xenobiotic-interacting protein. FEBS Lett 581, 3608-3615). Several independent studies involving AHR-deficient mice have revealed that AHR activation in response to endogenous ligands is involved in various signaling pathways important for normal cellular homeostasis, cellular differentiation and immune responses. Indeed, the AHR signaling pathway is known to be involved in the development and differentiation of immune cells, including not only T and B cells but also antigen-presenting cells such as dendritic cells and macrophages. Meaning and action of AHR in cancer progression or evidence for therapeutic potential of a selective AHR modulator with an antagonistic activity has been accumulated, confirming the possibility of AHR as a novel drug target for cancer therapy (Kolluri, S. K., Jin, U. H., and Safe, S. (2017) Role of the aryl hydrocarbon receptor in carcinogenesis and potential as an anti-cancer drug target. Arch Toxicol 91, 2497-2513).

Accordingly, the need for a cell line capable of screening the AHR modulator is emerging, and a mouse liver cancer cell line expressing EGFP (Enhanced GFP) under the control of an AHR-reactive promoter was reported as a conventional technology related to a cell line capable of screening the AHR modulator (Nagy, S R, Sanborn, J R, Hammock, B D, and Denison, M S (2002) Development of a green fluorescent protein-based cell bioassay for the rapid and inexpensive detection and characterization of ah receptor agonists Toxicol Sci 65, 200-210).

However, there are structural differences between human AHR and mouse AHR, indicating different interactions with heat-shock protein 90 (HSP90) and other cofactor. This leads to a 10-fold higher affinity of mouse AHR with TCDD compared to human AHR, and has the disadvantage that it may lead to overestimation of drug response in human application.

Korean Patent Publication No. 10-2019-0092898 discloses a transformed cell line in which cytochrome P450 is introduced into induced pluripotent stem cells, but it is difficult to obtain accurate data because it is necessary to measure the cytochrome P450 after killing the cells. Until now, there has been no disclosure of a screening method capable of selecting an AHR modulator using live human induced pluripotent stem cells introduced with cytochrome P450 conjugated with a fluorescent protein.

Accordingly, the present inventors constructed a human induced pluripotent stem cell line (hiPSC line) in which a gene was edited to express a cytochrome P450 1A1 protein in a state of fusion with a fluorescent protein without inhibiting its unique function by fusing a fluorescent protein gene to a gene coding the cytochrome P450 protein to perform AHR (aryl hydrocarbon receptor) screening through live-cell imaging in a living cell type. Then, the present inventors have completed the present invention by confirming that the AHR modulator can be screened in hepatocytes derived from the above cell line in a living state.

SUMMARY OF THE INVENTION

It is an object of the present invention to provide a human induced pluripotent stem cell line transformed with fluorescent protein-tagged cytochrome P450 for screening an AHR (aryl hydrocarbon receptor) modulator.

It is another object of the present invention to provide an AHR modulator screening method using the transformed human induced pluripotent stem cell line.

To achieve the above objects, the present invention provides a human induced pluripotent stem cell line (hiPSC line) transformed with fluorescent protein-tagged cytochrome P450 for screening an AHR (aryl hydrocarbon receptor) modulator.

In addition, the present invention provides an AHR modulator screening method comprising the following steps:

1) contacting a test substance to the human induced pluripotent stem cell line transformed with fluorescent protein-tagged cytochrome P450 protein;

2) measuring the signal intensity of the fluorescent protein in the human induced pluripotent stem cell line transformed with fluorescent protein-tagged cytochrome P450 protein contacted with the test substance; and 3) selecting a test substance that changes the signal intensity of the fluorescent protein compared to a control sample.

Advantageous Effect

The present invention relates to a human induced pluripotent stem cell line transformed with fluorescent protein-tagged cytochrome P450 and an AHR modulator screening method using the same. Specifically, a human-induced pluripotent stem cell line (hiPSC line) in which a gene was edited to express a cytochrome P450 protein in a state of fusion with a fluorescent protein without inhibiting its unique function was prepared, and it was confirmed that an AHR modulator involved in cytotoxicity and cancer development could be screened in the cell line-derived hepatocytes in a living state better than in the case of using existing Human primary hepatocytes (hPH) or HepG2 cells. Therefore, the human induced pluripotent stem cell line transformed with fluorescent protein-tagged cytochrome P450 of the present invention can be effectively used for screening AHR modulating compounds.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1b is a diagram showing the target position of three single-guide RNAs (sgRNAs) used to knock-in CYP1A1-mCherry.

FIG. 1d is a diagram showing the results of PCR analysis to confirm whether the mCherry knock-in vector was transfected into hiPSC cells.

FIG. 1e is a diagram showing the results of sequencing the junction sites between CYP1A1 and mCherry and between PGKneo and CYP1A1 in a CYP1A1-mCherry hiPSC cell line.

DESCRIPTION OF THE PREFERRED EMBODIMENTS

Figure 1A:
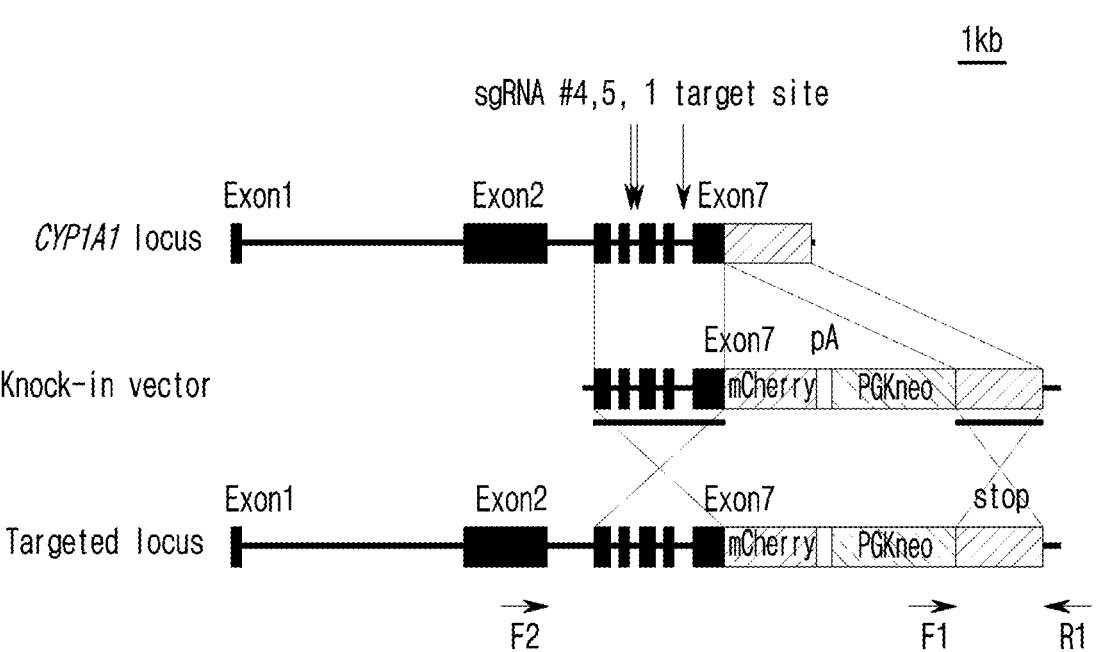
FIG. 1a is a diagram showing the schematic diagram of a vector used to prepare a CYP1A1-mCherry hiPSC cell line.

Hereinafter, the present invention is described in detail.

The present invention provides a human induced pluripotent stem cell line (hiPSC line) transformed with fluorescent protein-tagged cytochrome P450 for screening an AHR (aryl hydrocarbon receptor) modulator.

In the present invention, "induced pluripotent stem cells" can be cultured for a long time like embryonic stem cells, and can be differentiated into various somatic cells including nerve cells, hepatocytes, and cardiac cells, which are importantly used for drug metabolism and efficacy/toxicity tests.

The human induced pluripotent stem cell line was deposited at Korean Collection for Type Cultures (KCTC), Korea Research Institute of Bioscience and Biotechnology (KRIBB) under the accession number KCTC 14186BP.

The human induced pluripotent stem cells can be induced pluripotent stem cells derived from human skin fibroblasts.

The fluorescent protein can be selected from the group consisting of green fluorescence protein (GFP), cyan fluorescence protein (CFP), yellow fluorescence protein (YFP) and red fluorescence protein (DsRed), but is not limited thereto, preferably can be red fluorescent protein (DsRed), and more preferably mCherry protein.

In the present invention, "cytochrome P450 protein (CYP)" is a member of heme protein that promotes oxidation of foreign substances such as drugs, carcinogens and environmental pollutants and internal substrates such as steroids, fatty acids and vitamins, and various subtypes have been found in organs such as liver, kidney, intestinal tract and lung. Superfamily CYP enzymes, which are responsible for about 80% of drug oxidation metabolism, currently have 11 families known in the human body alone, of which 1 to 4 families are involved in drug metabolism, and more than 30 isozymes are known. There are three types of CYP isozymes known to be regulated by AHR: CYP1A1, CYP1A2 and CYP1B1.

The cytochrome P450 can be selected from the group consisting of CYP1A1, CYP1A2 and CYP1B1, but is not limited thereto, and is preferably CYP1A1. CYP1A2 is generally known to be expressed only in the liver of mature adults in the body, and is not suitable for screening because it is hardly expressed in cells differentiated from stem cells. CYP1B1 is known to have a higher expression level in blood cells than in liver cells, so it is not suitable for drug efficacy or toxicity tests.

In this invention, the term "transfection" is a method of modifying the genetic character of a cell by directly introducing DNA into a cultured animal cell, and a method of introducing a target gene into a medium such as a plasmid is generally used. The transfection can be performed according to the conventional method in the art, and preferably, can be performed by, for example, calcium phosphate co-precipitation, DEAE-dextran treatment, electroporation, redistribution method, or the like.

The targeting vector can typically be constructed as a vector for cloning or as a vector for expression. The targeting vector can be a conventional one used in the art to express a foreign protein in plants, animals or microorganisms. The targeting vector can be constructed through various methods known in the art. The targeting vector can be prepared by transfection using pMCDT-A vector, but is not limited thereto.

The human induced pluripotent stem cell line can be prepared by transfection with a vector into which a fluorescent protein is inserted using sgRNA targeting the genes represented by SEQ. ID. NO: 1 to NO: 3, but is not limited thereto.

In a specific embodiment of the present invention, the present inventors designed a targeting vector to knock-in a fluorescent protein into the cytochrome P450 locus in fibroblast-derived human induced pluripotent stem cells, and prepared a targeting vector using three single-guide RNAs (sgRNA) and transfected the human induced pluripotent stem cell line to establish a clone of a human induced pluripotent stem cell line transformed with fluorescent protein-tagged cytochrome P450 (see FIG. 1). As a result of confirming that the established transgenic human-induced pluripotent stem cell lines maintain the characteristics of human-induced pluripotent stem cells, it was confirmed that the pluripotent markers such as NANOG, OCT4, SOX2, TRA-1-60 and TRA-1-81 were normally expressed in human-induced pluripotent stem cells (see FIG. 2a). It was also confirmed that the possibility of cell differentiation into three germ layers through EB formation analysis (see FIGS. 2b and 2c). In addition, as a result of karyotype analysis of the prepared transgenic human induced pluripotent stem cell line, it was confirmed that the karyotype was normal (see FIG. 2d).

Therefore, it was confirmed that the human induced pluripotent stem cell line transformed with fluorescent protein-tagged cytochrome P450 prepared in the Example of the present invention maintained the characteristics of human induced pluripotent stem cells.

In addition, the present inventors confirmed the function of the hepatocytes differentiated from the human induced pluripotent stem cell line transformed with fluorescent protein-tagged cytochrome P450 prepared in the Example of the present invention. As a result, it was confirmed that the mRNA expression and protein expression of the hepatocyte-specific marker genes were increased (see FIGS. 4a to 4c), and albumin-positive hepatocytes were more than 96%, and it was confirmed that they were successfully differentiated into hepatocytes through albumin secretion detection and low-density lipoprotein-uptake analysis (see FIGS. 4d to 4g).

Figure 5A:
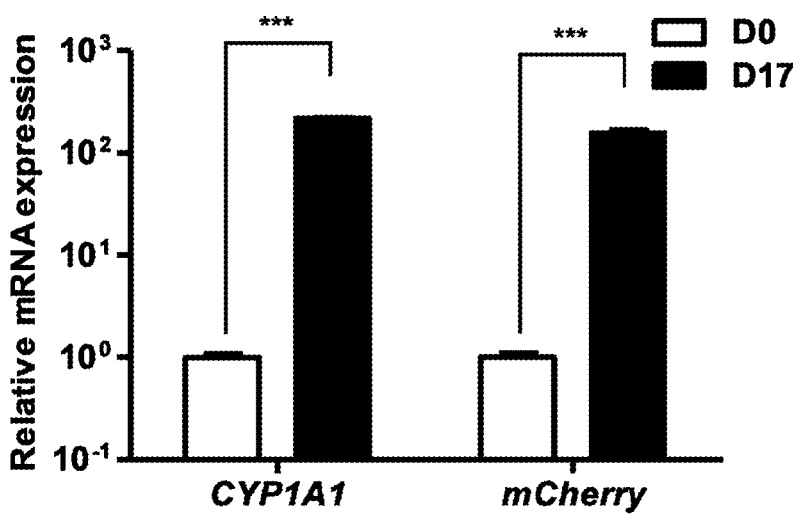
FIG. 5a is a diagram confirming the expression levels of CYP1A1 and mCherry mRNAs on days 0 and 17 in hepatocytes (CYP1A1-mCherry HLCs) differentiated from the CYP1A1-mCherry hiPSC cell line (N=6, *** $p<0.001$).

The present inventors confirmed the expression of fluorescent protein-tagged cytochrome P450 protein in the hepatocytes differentiated from the human induced pluripotent stem cell line transformed with fluorescent protein-tagged cytochrome P450 protein prepared in the Example of the present invention. As a result, it was confirmed that the fluorescent protein and cytochrome P450 were expressed at similar levels and were expressed at the same location (see FIG. 5).

The present inventors confirmed whether a signal of a fluorescent protein could be induced by an AHR agonist. As a result, it was confirmed that the intensity of the fluorescent protein was increased in proportion to the activity of cytochrome P450 when the hepatocytes differentiated from the human induced pluripotent stem cell line transformed with fluorescent protein-tagged cytochrome P450 were treated with a known AHR agonist (see FIGS. 6 to 7).

From the above results, it was confirmed that the hepatocytes differentiated from the human induced pluripotent stem cell line transformed with fluorescent protein-tagged cytochrome P450 of the present invention can be used for screening of an AHR modulator.

In addition, the present invention provides an AHR modulator screening method comprising the following steps:

1) contacting a test substance to the human induced pluripotent stem cell line transformed with fluorescent protein-tagged cytochrome P450 protein;

2) measuring the signal intensity of the fluorescent protein in the human induced pluripotent stem cell line transformed with fluorescent protein-tagged cytochrome P450 protein contacted with the test substance; and 3) selecting a test substance that changes the signal intensity of the fluorescent protein compared to a control sample.

The control sample of step 3) can be BaP or TCDD, but is not limited thereto.

The AHR modulator screening method can be performed in a high content screening system (HCS).

In a specific embodiment of the present invention, the present inventors set up an automatic analysis protocol with a high-content screening (HCS) device using the hepatocytes derived from the prepared human-induced pluripotent stem cell line transformed with fluorescent protein-tagged cytochrome P450 and screened an AHR modulator. As a result, three compounds that increase the fluorescent protein expression and two compounds that decrease the fluorescent protein expression were selected (see FIGS. 8 to 10).

In addition, the present inventors compared the hepatocytes derived from the prepared human induced pluripotent stem cell line transformed with fluorescent protein-tagged cytochrome P450 and hPH and HepG2 cell lines. As a result, it was confirmed that the hepatocytes derived from the prepared human induced pluripotent stem cell line transformed with fluorescent protein-tagged cytochrome P450 could be used as living conditions, and thus more suitable for the AHR screening method than hPH and HepG2 cells (see FIGS. 11 to 13).

Currently commercially available AHR reporter cell lines are based primarily on a luciferase reporter system under the control of a CYP1A1 promoter in several malignant cell lines such as HepG2 (liver cancer cells) and HT29 (colorectal adenocarcinoma cells). Treatment of BaP in HepG2 cells causes undesirable gene elevation and pathway activation. Human primary hepatocytes (hPH) show an excellent effect in terms of response to BaP, but cell supply is limited as cells are no longer divided. On the other hand, the transformed human induced pluripotent stem cell line-derived hepatocytes of the present invention have the advantages of the induced pluripotent stem cells themselves, which can provide cells with potential for future cell differentiation and provide various cell types.

Although a luciferase-based AHR reporter human induced pluripotent stem cell line (hiPSCs) has also been reported (Smith, B W, Stanford, E A, Sherr, D H, and Murphy, G J (2016) Genome Editing of the CYP1A1 Locus in iPSCs as a Platform to Map AHR Expression throughout Human Development Stem Cells Int 2016, 2574152), the luciferase reporter system entails cell sacrifice to investigate AHR activity, while the reporter system of the present invention has the advantage of exhibiting AHR activity in living cells through the fluorescence level of CYP1A1-mCherry. As a result, it is possible to track not only the concentration of the drug but also the reaction kinetics according to the drug treatment time in the same cell, providing additional information for understanding the drug mechanism.

Hereinafter, the present invention will be described in detail by the following examples.

However, the following examples are only for illustrating the present invention, and the contents of the present invention are not limited thereto.

<Experimental Methods>

1. Culture of Human Induced Pluripotent Stem Cells and Differentiation into Hepatocytes Human-induced pluripotent stem cells (hiPSC) derived from human skin fibroblasts were used in knock-in experiments as the control human-induced pluripotent stem cells (hiPSC).

First, human-induced pluripotent stem cells derived from human skin fibroblasts were maintained in mTeSR-E8 medium containing Vitronectin XF™ (Stem Cell Technologies, Vancouver, Canada) and dissociated every 3 or 4 days using 0.5 mM EDTA in DPBS (Dulbecco's Phosphate-Buffered Saline).

The following experiment was performed to differentiate the cultured hiPSCs into hepatocytes. Specifically, hiPSCs were plated on Matrigel® (Corning, Tewksbury, Mass., USA) coated culture dishes and cultured in mTeSR™-E8™ (Stem Cell Technologies) for 1 day. For the differentiation of definitive endoderm (DE), hiPSCs were cultured for 1 day in RPMI-1640 containing 0.5 mg/ml of bovine serum albumin (BSA), 2% B27 (Thermo Fisher Scientific, Waltham, Mass., USA), 50 ng/ml of activin A (Peprotech, Rocky Hill, N.J., USA) and 1 mM sodium butyrate (Sigma-Aldrich, St. Louis, Mo., USA). Then, cell culture was continued for 4 days in the same medium in which the concentration of sodium butyrate was reduced. Next, DE cells were differentiated into hepatic endodermal cells by culturing in RPMI-1640 containing 0.5 mg/ml of BSA, 2% B27, 10 ng/ml of fibroblast growth factor 4 (FGF4, Peprotech) and 10 ng/ml of hepatocyte growth factor (HGF, Peprotech) for 5 days. Liver maturation was induced by culturing the cells in a hepatocyte culture medium (HCM; Lonza, Basel, Switzerland) supplemented with 10 ng/ml of FGF4, 10 n/ml of HGF, 10 ng/ml of oncostatin M (Peprotech) and 0.1 μM dexamethasone (Sigma-Aldrich) for 7 days. The culture medium was replaced every day.

For the formation of embryoid body (EB), CYP1A1-mCherry hiPSCs were dissociated using 0.5 mM EDTA and seeded on AggreWell™ 800 plates (Stem Cell Technologies). On the next day, the cell aggregate was transferred to low adhesion plates and cultured in mTeSR™-E8™ medium for 7 days. The formed embryoid body was cultured on a Matrigel®-coated plate for an additional 7 days prior to analysis.

Human primary hepatocytes (Corning, Donor No. 303) were plated on a collagen I-coated culture plate using Gentest™High Viability CryoHepatocyte Recovery kit (Corning) according to the manufacturer's instructions, and an experiment was performed 24 hours later. HepG2 cells were cultured in Eagle's Minimum Essential Medium (EMEM; Biowest, Nuaille, France) containing 10% fetal bovine serum (FBS; Thermo Fisher Scientific).

2. mCherry Knock-In Using CRISPR-Cas9 System

Human codon-optimized SpCas9 and chimeric guide RNA expression plasmid (pX330-U6-Chimeric_BB-CBh-hSpCas9; Addgene, Watertown, Mass., USA) were used to target vector construction. A single guide RNA (sgRNA) was constructed using an online CRISPR design tool at the intron site of the target gene. The sgRNA was selected using the lowest off-target effect. The target sequences of the three single guide RNAs (sgRNAs) are shown in Table 1 below. The following experiment was performed according to the target sequence cloning protocol of the Zhang's laboratory.

TABLE 1

| Locus | sgRNA | Score | Target site | | PCR analysis colony | Freeze | SEQ. ID. NO: |
|-------|-------|-------|-------------|-----|-----|--------|-----|
| E6-E7_intron | Guide #1 | 78 | GCATTGATCC TCCTGTCCAT | GGG | 6 /13 | 5 | 1 |
| E4-E5_intron | Guide #4-2 | 73 | TAGGTAGTGG CTCCCTTCAA | AGG | 12 /29 | 9 | 2 |
| | Guide #5_Reverse | 73 | CTGGCACTGA CCCCTTTGAA | GGG | 4 /9 | 3 | 3 |

The pMCDT-A vector was used as the backbone of the targeting vector. The human CYP1A1 gene was amplified by polymerase chain reaction (PCR) using genomic DNA extracted from hiPSCs. 5' and 3' homologous arms were targeted 1.2 kb upstream and 0.93 kb downstream of the stop codon in CYP1A1, respectively. mCherry and PGKneo were amplified by PCR from the plasmids containing them. After sequence confirmation, each fragment was ligated using a T4 DNA ligase (Promega, Madison, Wis., USA). 5' homologous arms, mCherry, PGKneo and 3' homologous arms were ligated using SmaI, HindIII and SalI, respectively. The resulting final fragment was inserted into pMCDT-A vector using NotI and XhoI. For transfection, hiPSCs at passage 28 were prepared as single cells ($2.5 \times 10^7$ cells/ml) by dissociation with 0.5 mM EDTA in DPBS. 4 μg of the targeting vector and 1 μg of the Cas9 vector were added to the cell suspension and electroporation was performed under the conditions of 1600 V, 20 ms, and 1 pulse using NEON® (Invitrogen, Carlsbad, Calif., USA) transfection system. After the electroporation, cells were seeded on a Matrigel®-coated 48-well plate at the density of 1,000 viable cells/well. The cells were expanded for 48 hours and then selected with 50 μg/ml of Geneticin (G418 sulfate, Gibco) for 2 weeks. Thereafter, drug-resistant clones were manually selected, and expansion and further experiments were performed. For the analysis of the present invention, CYP1A1-mCherry hiPSCs from passages 29 to 40 were used.

3. Characteristic Analysis of CYP1A1-mCherry hiPSC Line

To confirm the genome targeting efficiency, T7 endonuclease I analysis was performed according to the manufacturer's protocol.

Specifically, genomic DNA was extracted from hiPSCs transfected with or without sgRNA using G-spin™Total Genomic DNA Extraction Kit (Intron Biotechnology, Gyeonggi, Korea). Then, a 500 bp fragment containing the sgRNA binding site was amplified by PCR. After purifying the PCR product using MEGAquick-spin™Plus Total Fragment DNA purification kit (Intron Biotechnology), the product was denatured and annealed and then digested with T7 endonuclease I (NEB, Ipswich, Mass., USA). The digested DNA fragments were analyzed by agarose gel electrophoresis. Knock-in was confirmed by PCR and DNA sequencing of the targeted integration site. Genomic DNA was isolated from drug-resistant clones using a G-DEX genomic DNA extraction kit (Intron Biotechnology), and 50 ng of the isolated DNA was amplified using EX Taq® polymerase (Takara Bio, Shiga, Japan) with the primers listed in Table 2.

To analyze the karyotype of CYP1A1-mCherry hiPSC, G-banding karyotype analysis (GenDix, Seoul, Korea) was performed with a band resolution of 550 for 20 single clones.

TABLE 2

| Primer | Sequence (5'→3') | SEQ. ID. NO: |
|---|---|---|
| CYP1A1 forward | AGGCTTTTACATCCCCAAGG | 4 |
| CYP1A1 reverse | TTGTCGATAGCACCATCAGG | 5 |
| mCherry forward | GTGAGCACTTCCAAATGCAGC | 6 |
| mCherry reverse | CCTTGAAGCGCATGAACTCCT | 7 |
| PAX6 forward | GTGTCCAACGGATGTGTGAG | 8 |
| PAX 6 reverse | CTAGCCAGGTTGCGAAGAAC | 9 |
| OTX2 forward | TGCAGGGGTTCTTCTGTGAT | 10 |
| OTX2 reverse | AGGGTCAGAGCAATTGACCA | 11 |
| α-SMA forward | TGCTCTGGGTTCGTCAGAGTC | 12 |
| α-SMA reverse | CAGGCAAGTCACTGTGTGGC | 13 |
| EOMES forward | AGGCGCAAATAACAACAACAC | 14 |
| EOMES reverse | ATTCAAGTCCTCCACGCCATC | 15 |
| Brachyury forward | GCGGGAAAGAGCCTGCAGTA | 16 |
| Brachyury reverse | TTCCCCGTTCACGTACTTCC | 17 |
| FOXA2 forward | ATGCACTCGGCTTCCAGTAT | 18 |
| FOXA2 reverse | CACGTACGACGACATGTTCA | 19 |
| GATA4 forward | TCCAAACCAGAAAACGGAAG | 20 |
| GATA4 reverse | CTGTGCCCGTAGTGAGATGA | 21 |
| SOX17 forward | CAGAATCCAGACCTGCACAA | 22 |
| SOX17 reverse | GCGGCCGGTACTTGTAGTT | 23 |
| ALB forward | GAGACCAGAGGTTGATGTGATG | 24 |
| ALB reverse | AGTTCCGGGGCATAAAGTAAG | 25 |
| AAT forward | GAAGTCAAGGACACCGAGGA | 26 |
| AAT reverse | GCTGGCAGACCTTCTGTCTT | 27 |
| TDO2 forward | CAAATCCTCTGGGAGTTGGA | 28 |
| TDO2 reverse | GTCCAAGGCTGTCATCGTCT | 29 |
| HNF4A forward | CGAGCAGATCCAGTTCATCA | 30 |
| HNF4A reverse | TCACACATCTGTCCGTTGCT | 31 |

12

TABLE 2-continued

| Primer | Sequence (5'→3') | SEQ. ID. NO: |
|---|---|---|
| G6Pase forward | TCAACCTCGTCTTTAAGTGGATTCT | 32 |
| G6Pase reverse | AGTATACACCTGCTGTGCCC | 33 |
| TAT forward | GCTTCCTCAAGTCCAATGCT | 34 |
| TAT reverse | CTGTGATGACCACTCGGATG | 35 |
| TTR forward | ACCGGTGAATCCAAGTGTCC | 36 |
| TTR reverse | GGTTTTCCCAGAGGCAAATGG | 37 |
| AFP forward | AGCTTGGTGGTGGATGAA | 38 |
| AFP reverse | TCTGCAATGACAGCCTCAAG | 39 |

4. Flow Cytometry

HLCs derived from CYP1A1-mCherry hiPSCs were dissociated with 0.5 mM EDTA and washed with DPBS containing 10% FBS. The dissociated cells were fixed and permeabilized with Foxp3 fixation/permeabilization solution (eBioscience, San Diego, Calif., USA) for 1 hour at room temperature (RT). The cells were incubated with 1 μg of mouse anti-ALB primary antibody (R & D Systems, Minneapolis, Minn., USA) for 1 hour and then tagged with fluorescein-conjugated secondary antibody for 1 hour on ice. Flow cytometry was performed using a FACSCalibur™ flow cytometer (BD Biosciences, San Jose, Calif., USA) and data was analyzed with FlowJo® software.

5. Hepatic Functional Tests

In the case of enzyme-linked immunosorbent assay (ELISA), the culture supernatant was collected 24 hours after the medium was replaced, and the amount of the secreted albumin was measured using a human albumin ELISA quantification kit (Bethyl Laboratories, Montgomery, Tex., USA) according to the manufacturer's protocol. The amount of the secreted albumin was measured using 100 μl of the culture supernatant from an independent culture dish, calculated according to each standard curve, and normalized to protein content. The protein content was determined using a Bio-Rad protein analysis kit (Bio-Rad, Hercules, Calif., USA). For acetylated-low density lipoprotein (Ac-LDL) absorption analysis, cells were cultured with 10 μg/ml of 1,1'-dioctadecyl-3,3,3',3'-tetramethylindocarbocyanine-tagged Ac-LDL (Life Technologies, Carlsbad, Calif., USA) for 5 hours. Red fluorescence was visualized with a fluorescence microscope.

6. Immunocytochemical Analysis

Cells were fixed using 4% formaldehyde (Sigma-Aldrich) for 30 minutes at room temperature, and then washed three times with PBS containing 0.1% Tween 20 (PBST) for 10 minutes. Then, the samples were permeabilized for 15 minutes in PBS containing 0.1% Triton X-100 (Sigma-Aldrich), and blocked with 4% normal goat serum (Jackson ImmunoResearch, West Grove, Pa., USA) for 1 hour at RT. The cells were diluted in PBS containing 4% normal sheep serum (for SOX17) or normal goat serum (for others) and then cultured overnight at 4° C. with the following primary antibodies: rabbit anti-CYP1A1 (1:200; Abcam, Cambridge, UK), mouse anti-mCherry (1:200), rabbit anti-AAT (1:200), mouse anti-HNF4A (1:200; Abcam), rabbit anti-ALB (1:50), rabbit anti-AFP (1:200; Dako, Glostrup, Denmark), rabbit anti-OCT4 (1:400), rabbit anti-NANOG (1:400; Cell Signaling Technology, Danvers, Mass., USA), mouse anti-SOX2 (1:50; Santa Cruz Biotechnology, Dallas, Tex., USA), mouse anti-TRA-1-60 (1:100), mouse anti-TRA-1-81 (1:100), mouse anti-Nestin (1:200), rabbit anti-Desmin (1:50; Millipore, Burlington, Mass., USA), mouse anti-SMA (1:500; Sigma-Aldrich), goat anti-SOX17 (1:50; R & D Systems) and rabbit anti-TUBB3 (1:1000; BioLegend, San Diego, Calif., USA). The cells were washed 6 times in PBST for 10 minutes each, and the cells were incubated at room temperature for 1 hour with appropriate secondary antibodies diluted in PBST as follows: Alexa Fluor 488, 594 goat anti-mouse IgG, Alexa Fluor 594 goat anti-rabbit IgG or Alexa Fluor 488 chicken anti-goat IgG (1:200; Thermo Fisher Scientific). The cells were then washed with PBST and stained with 4'-6-diamidino-2-phenylindole (DAPI, Sigma-Aldrich) for visualization of nuclei. Endoplasmic reticulum (ER) was marked using ER Tracker™Green (Invitrogen) according to the manufacturer's protocol.

7. Ethoxyresorufin-O-Deetylase (EROD) Analysis

To measure the CYP1A1 activity, cells were cultured in a serum-free medium for 24 hours before treatment. The cells were treated with 7.5 μM ethoxyresorufin in the presence or absence of 10 μM dicumarol (inhibitor) in HBSS for 7.5, 15, 30 and 60 minutes, and 100 μl of the medium was removed into a new microcentrifuge tube. The same amount (100 μl) of ice-cold acetonitrile-methanol was added to the removed medium, followed by brief vortexing and centrifugation at 16,000×g for 5 minutes at 4° C. The supernatant was used for the following analysis. The level of the metabolite resorufin was measured by high-performance liquid chromatography (HPLC) with a Luna C18 column (4.6×150 mm, 5 μm; Phenomenex, Seoul, Korea). The moving phase was composed of 20 mM phosphate buffer-methanol-acetonitrile (52:45:3, v/v/v), and the flow rate was 0.8 ml/minute. Fluorescence was measured at an excitation wavelength of 560 nm and an emission wavelength of 585 nm. Concentrations were calculated using a standard curve for resorufin normalized by the total cellular protein content measured using a BCA protein analysis kit (Thermo Fisher Scientific).

8. Quantitative Reverse Transcription PCR (RT-qPCR)

Total RNA was extracted from each sample using Nucleo-ZOL reagent (Macherey-Nagel, Duren, Germany) and reverse transcription was performed using GoScript™ reverse transcription mix (Promega) according to the manufacturer's protocol. RT-qPCR was performed with SYBR Green Realtime PCR Master Mix (TOYOBO, Osaka, Japan) in StepOnePlus Real-Time PCR system (Applied Biosystems, Foster City, Calif., USA). PCR amplification was performed in triplicate for each sample. PCR results were expressed as relative fold change compared to the control cells after normalization with glyceraldehyde-3-phosphate dehydrogenase (GAPDH). The ΔCt (SΔCt) value was calculated as the difference between the Ct value obtained for GAPDH and the target gene. The ΔCt value of the control cells was used as the control ΔCt (CΔCt) value. The relative gene expression level was determined using the following formula: 2−(SΔCt−CΔCt). The primers used in the experiment are shown in Table 2.

9. Chemical Treatment and High-Content Screening (HCS)

To perform HCS, the cells differentiated for 10 days were dissociated, plated in a Matrigel®-coated 96-well plate, and cultured for maturation. After 24 hours of completion of differentiation, the cells were treated with 241 chemicals including hepatotoxicity library (SCREEN-WELL® Hepatotoxicity library; Enzo Life Sciences, Farmingdale, N.Y., USA) and nuclear receptor ligands library (SCREEN-WELL® Nuclear Receptor Ligands Library; Enzo Life Sciences), and AHR agonists (2,3,7,8-tetrachlorodibenzo-p-dioxin (TCDD) and benzo[a]pyrene (BaP)) as positive controls for 24 and 48 hours. DMSO was used as a vehicle control. For staining the live cell nucleus, cells were cultured with 2 μg/ml of Hoechst 33342 (Life Technologies) for 10 minutes. Stained cells were imaged using ImageXpress Micro XLS Widefield High-Content Analysis System (Molecular Devices, San Jose, Calif., USA). The acquired images were analyzed using MetaXpress High-Content Image Acquisition and Analysis Software (Molecular Devices) according to disclosed methods. For analysis, cells were first identified using Hoechst staining and mCherry intensity was detected to measure CYP1A1 expression. All chemical concentrations used for screening were 10 μM except TCDD (10 nM), BaP (1 μM) and H01 (3-methylcholanthrene; 1 μM).

10. Dose-Response Curve

To measure a dose-response curve, the samples were incubated at individual concentrations for 24 hours with TCDD, BaP, papaverine hydrochloride, nordihydroguaret acid and glafenine. To measure dose-response curves, the samples were incubated with TCDD, BaP, papaverine hydrochloride, nordihydroguaretic acid and glafenine at individual concentrations (TCDD at concentrations of 0.1, 1, 10, and 50 μM and other compounds at concentrations of 0.01, 0.1, 1, 10, 50, and 100 μM) for 24 hours. After preparing cells for RNA extraction, RT-qPCR analysis for the expression of CYP1A1 mRNA was performed according to the above procedure. Dose-response curves were created by the least squares fitting method using GraphPad Prism 5 (GraphPad, San Diego, Calif., USA). The samples with low RNA concentration (<50 μg/ml) due to cell death were recovered.

11. Cell Viability Analysis

To analyze cell viability, target chemicals (10 μM) were treated for 24 hours prior to performing cell viability analysis. Then, 10 μl of cell counting Kit-8 was added to 100 μl of the medium, followed by incubation for 2 hours. Absorbance was measured at 450 nm using an iMark™ microplate absorbance reader (Bio-Rad). Cell viability was calculated using the following formula:

$$\text{Cell viability } (\%) = (A_{sample} - A_{blank})/(A_{control} - A_{blank}) \times 100$$

12. Microarray Analysis

For microarray analysis, total RNA samples of hiPSC-derived hepatocytes, and HepG2 and human primary hepatocytes (hPH) treated with or without 1 μM BaP were prepared using TRIzol reagent. Microarray analysis was performed using Agilent Human GE 4×44 V2 chip (Agilent, Santa Clara, USA) by a service provider (eBiogen, Seoul, Korea).

Gene ontology and KEGG pathway analysis was performed using DAVID with selection of gene ontology (Biological process, Molecular function, and Cellular components) and KEGG pathway. Principal component analysis (PCA), mean Z-score calculation, R-square and correlation plots were performed and visualized using R (v.3.6.1).

13. Statistical Analysis and Visualization

Graph visualization and statistical analysis of RT-qPCR, CYP1A1 activity and mCherry measurements were performed using GraphPad Prism 5 and Microsoft Excel (Redmond, Wash., USA). Chemical structures were drawn using MarvinSketch (v20.6; ChemAxon, Budapest, Hungary).

<Example 1> Preparation of mCherry Knock-In Vector Using CRISPR-Cas9 System

Figure 1C:
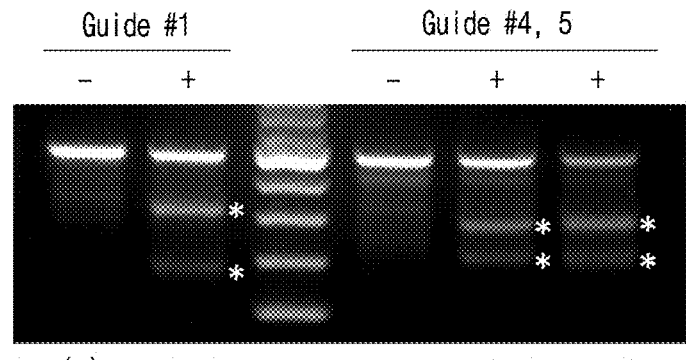
FIG. 1c is a diagram showing the results of investigating the efficiency of three sgRNAs by T7 endonuclease I analysis.

In order to establish a live monitoring system of AHR activity in hiPSCs, CYP1A1 transcriptionally regulated by AHR was targeted. To minimize the off-target effect of a fluorescent marker insertion, HR-mediated knock-in was induced in the target gene locus using the CRISPR-Cas9 system by the method described in <Experimental Methods>2. A targeting vector was designed to knock-in mCherry into the CYP1A1 gene locus in pre-established hiPSCs derived from normal fibroblasts (FIG. 1a). mCherry cDNA was inserted at the end of the last exon of CYP1A1 with a deletion of the stop codon. Phospho glycerate kinase (PGK)-neo and diphtheria toxin A (DT-A) were included in targeting vectors for positive and negative selection, respectively. Three single-guide RNAs (sgRNAs) were directed to target exon 4-exon 5 (E4-E5) or exon 6-exon 7 (E6-E7) introns (FIG. 1b). The efficiency of sgRNA was investigated by T7 endonuclease I analysis, and it was confirmed that all sgRNAs effectively induced DNA cleavage, resulting in indels more than 50% (FIG. 1c).

Figure 1D:
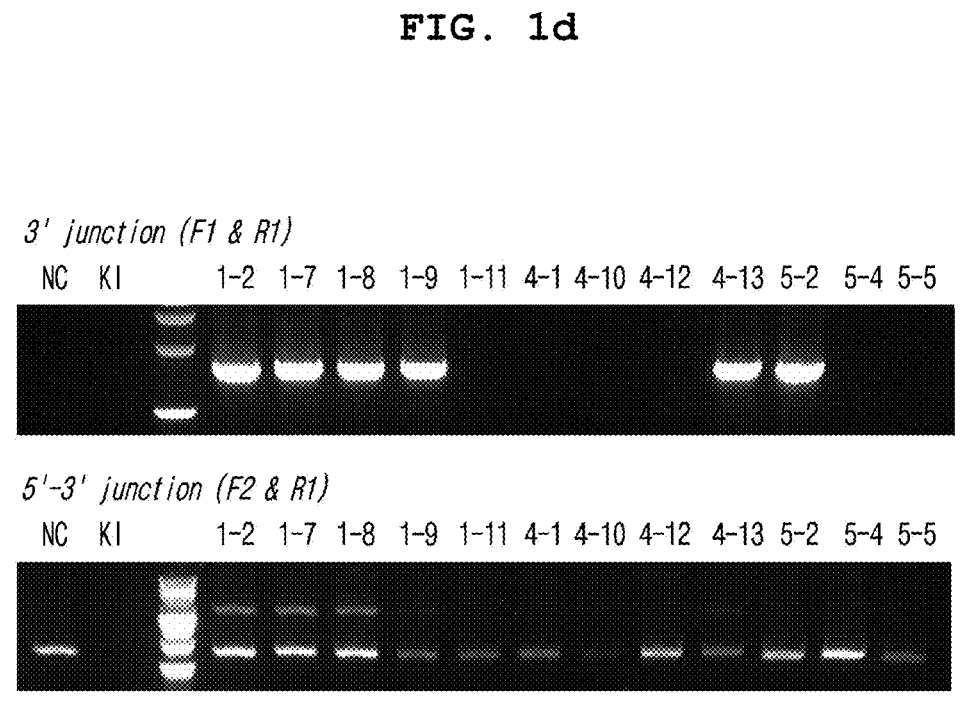
Figure 1E:
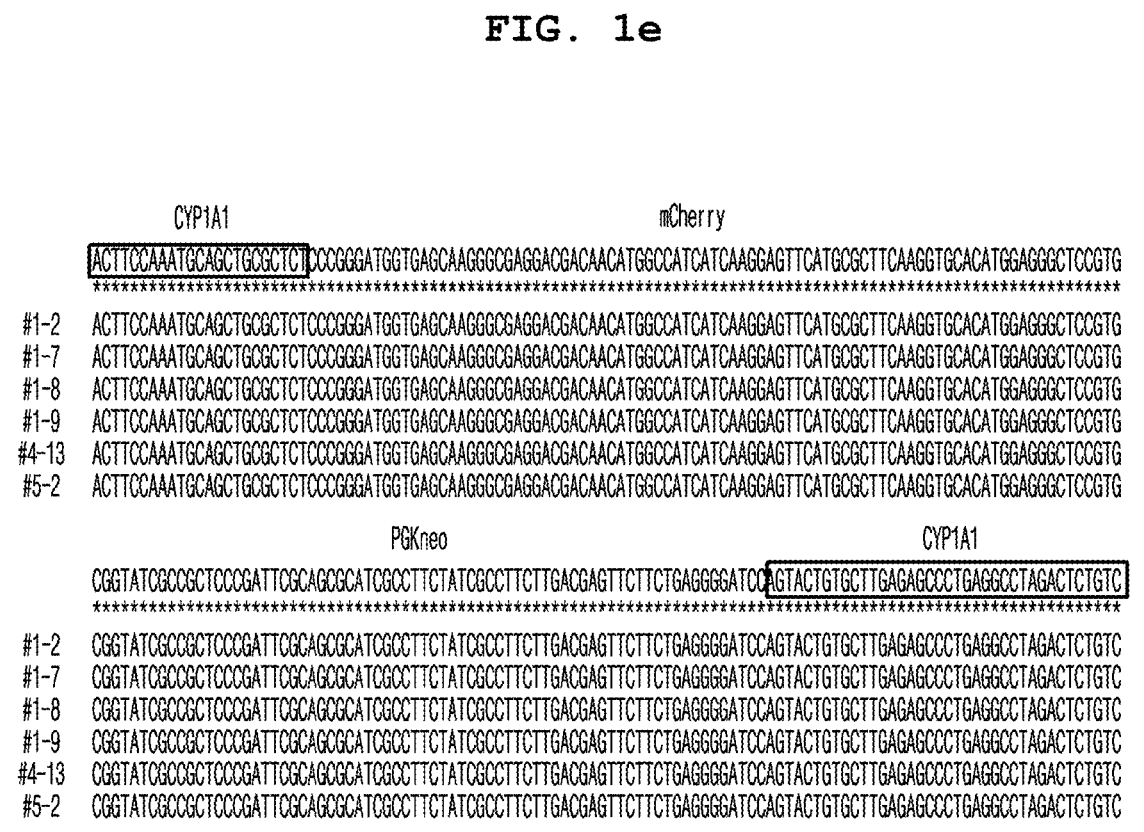

HiPSCs were transfected with a targeting vector containing Cas9 and individual sgRNA. For positive selection, the transfected hiPSCs were treated with G418, followed by single cell clone expansion. Modification of the target gene locus in the proliferating cells during the clone expansion was confirmed by PCR with the primer set shown in FIG. 1a (FIG. 1d). In order to confirm the integration of the cassette at the designated site, the results of sequencing the junction between CYP1A1 and mCherry and between PGKneo and CYP1A1 are shown in FIG. 1e (FIG. 1e).

As a result of the above experiment, six clones (#1-2, #1-7, #1-8, #1-9, #4-13 and #5-2) of the hiPSC line expressing mCherry-fused CYP1A1 were established and deposited at Korean Collection for Type Cultures (KCTC), Korea Research Institute of Bioscience and Biotechnology (KRIBB) under the accession number KCTC 14186BP.

<Experimental Example 1> Confirming Whether CYP1A1-mCherry hiPSCs Retain Characteristics of hiPSCs Line #1-8 was selected as a line to be used in the experiment to determine whether CYP1A1-mCherry hiPSCs maintain the characteristics of hiPSCs. To investigate whether the CRISPR-Cas9-mediated gene editing affects the characteristics of hiPSCs, pluripotency and genomic stability characteristics were examined in CYP1A1-mCherry hiPSCs by the method described in <Experimental Methods>3.

Figure 2A:
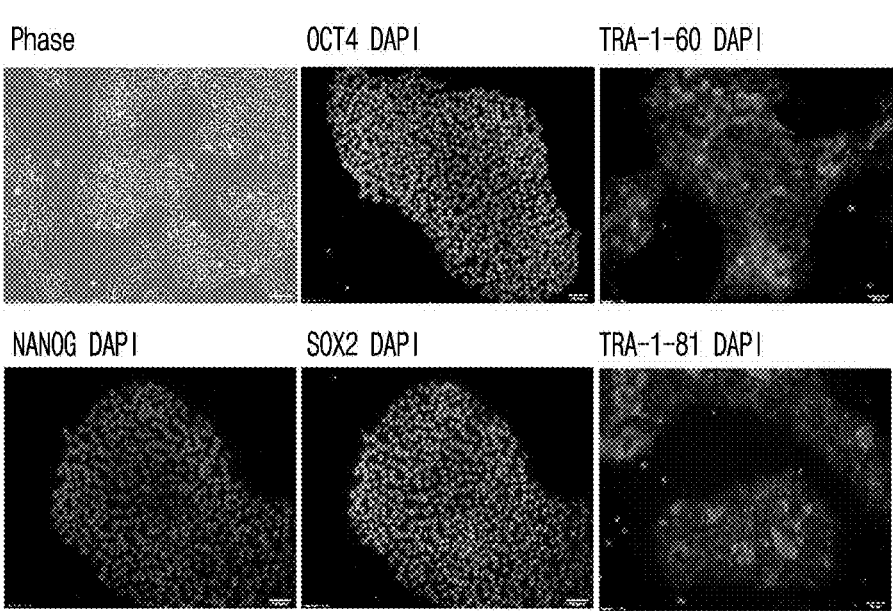
FIG. 2a is a diagram showing the results of confirming the expression of hiPSC markers such as NANOG, OCT4, SOX2, TRA-1-60 and TRA-1-81 using fluorescence immunostaining.
Figure 2B:
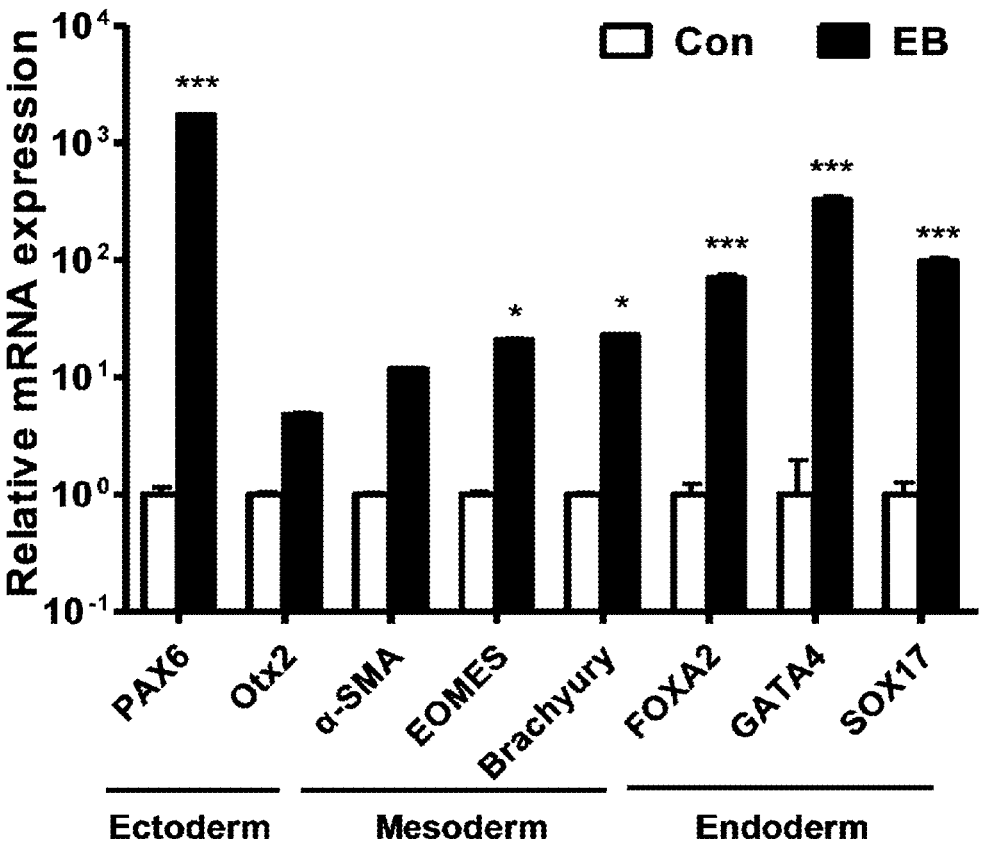
FIG. 2b is a diagram showing the results of confirming the expression of mRNAs of three germline marker proteins after differentiation of hiPSC into various cells corresponding to the embryonic three germ layers.
Figure 2C:
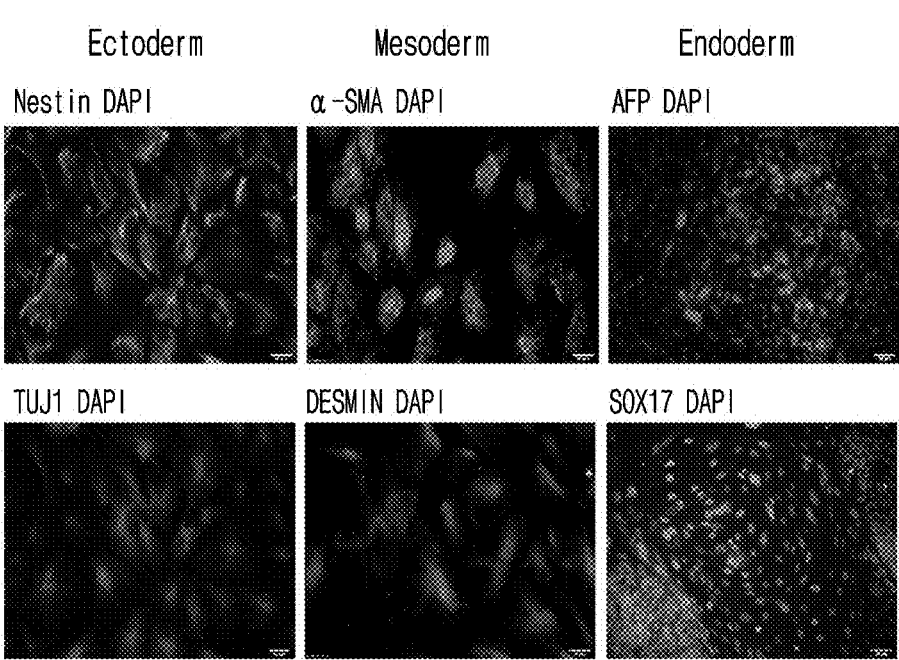
FIG. 2c is a diagram showing the results of confirming the expression of three germline marker proteins using fluorescence immunostaining after differentiation of hiPSC into various cells corresponding to three embryonic germ layers.
Figure 2D:
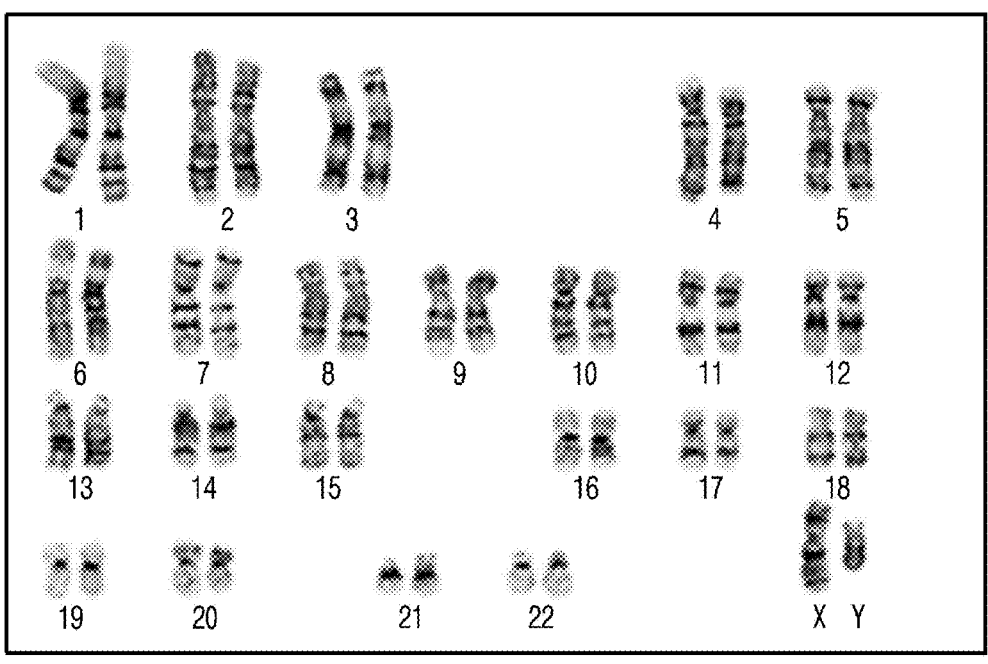
FIG. 2d is a diagram showing the results of investigation through karyotype analysis whether an abnormality occurs in the entire chromosome of the cell due to the introduction of mCherry DNA.

As a result, as shown in FIG. 2a, the pluripotency markers such as NANOG, OCT4, SOX2, TRA 60 and TRA-1-81 were expressed in the line #1-8 (FIG. 2a). The possibility of cell differentiation into three germ layers was confirmed through EB formation assay. EB expressed all three germ layer markers at the mRNA (FIG. 2b) and protein (FIG. 2c) levels. In addition, as a result of confirming the karyotype of CYP1A1-mCherry hiPSCs, it was confirmed that the karyotype of the hiPSCs was normal (FIG. 2d).

From the above results, it was confirmed that the mCherry knock-in process induced by the CRISPR-Cas9 system did not affect the pluripotency of CYP1A1-mCherry hiPSCs.

Figure 3:
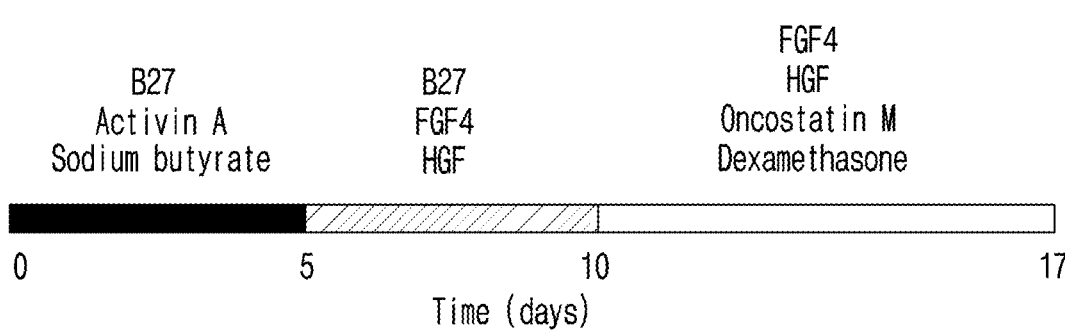
FIG. 3 is a diagram showing the stepwise direct differentiation protocol for differentiating the CYP1A1-mCherry hiPSC cell line into hepatocytes.

<Experimental Example 2> Confirmation of Function of Hepatocytes Differentiated from CYP1A1-mCherry hiPSCs CYP1A1 and its upstream regulator, the aryl hydrocarbon receptor (AHR), are involved in phase I xenobiotic and drug metabolism in the liver. Anticipating that the CYP1A1-mCherry hiPSC line could be used for compound and drug screening through hepatocyte differentiation, CYP1A1- mCherry hiPSCs were differentiated into hepatocytes by the stepwise direct differentiation protocol shown in FIG. 3 (FIG. 3). Then, the function of the differentiated hepatocytes was confirmed by the methods of <Experimental methods> 4, 5 and 6.

Figure 4A:
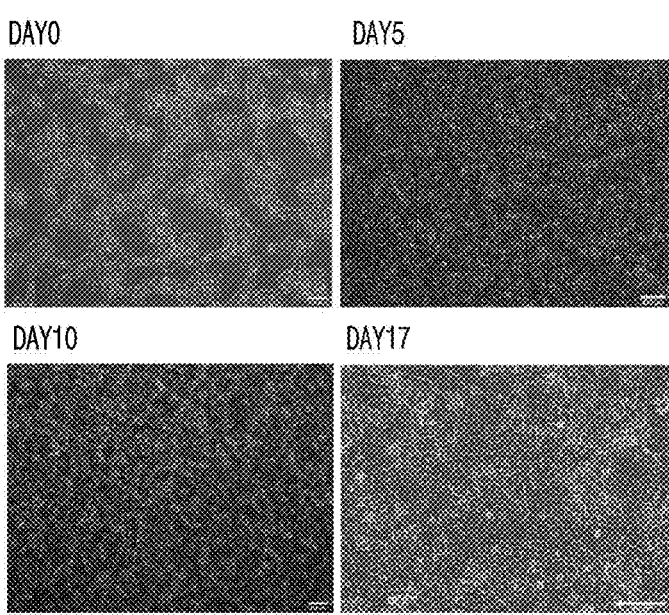
FIG. 4a is a diagram showing the results of observing the morphology of the hepatocytes differentiated from the CYP1A1-mCherry hiPSC cell line.

First, as a result of observing the cell morphology, as shown in FIG. 4a, the cell morphology was changed as follows at each stage of differentiation: definitive endoderm on day 5, liver progenitors on day 10, and hepatocytes on day 17 (FIG. 4a).

Figure 4B:
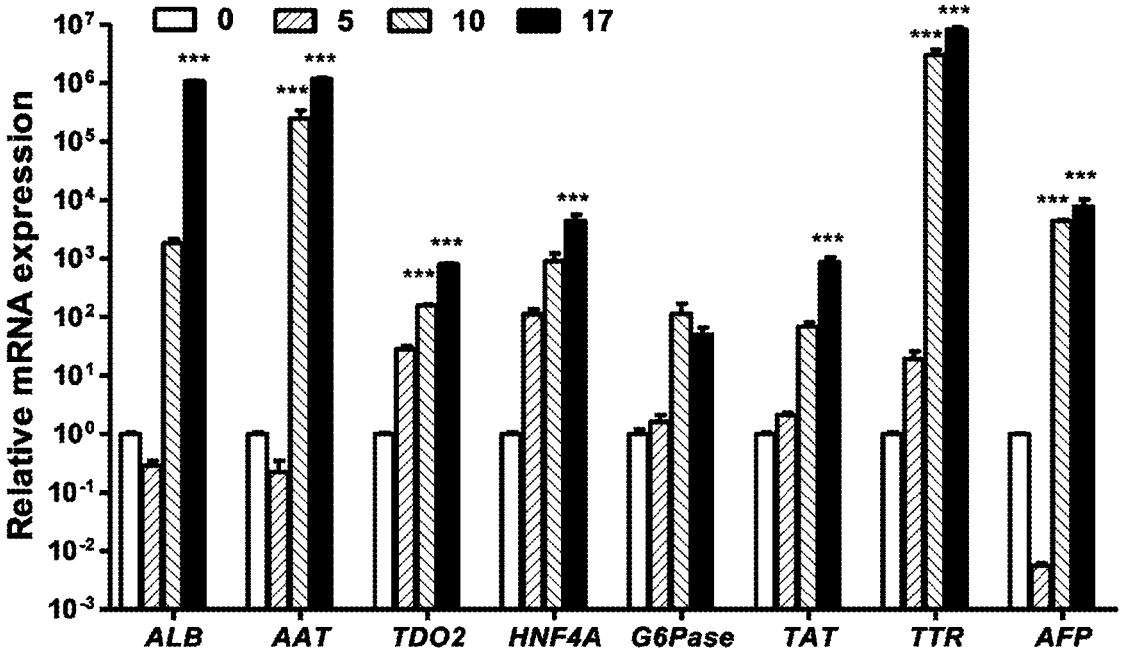
FIG. 4b is a diagram confirming the expression of mRNAs of hepatocyte-specific marker genes such as ALB, AAT, TDO2, HNF4A, G6Pase, TAT, TTR and AFP in the hepatocytes differentiated from the CYP1A1-mCherry hiPSC cell line.

It was confirmed that the transcriptional expression of hepatocyte-specific marker genes such as ALB, AAT, TDO2, HNF4A, G6Pase, TAT, TTR and AFP was increased with the differentiation (FIG. 4b).

Figure 4C:
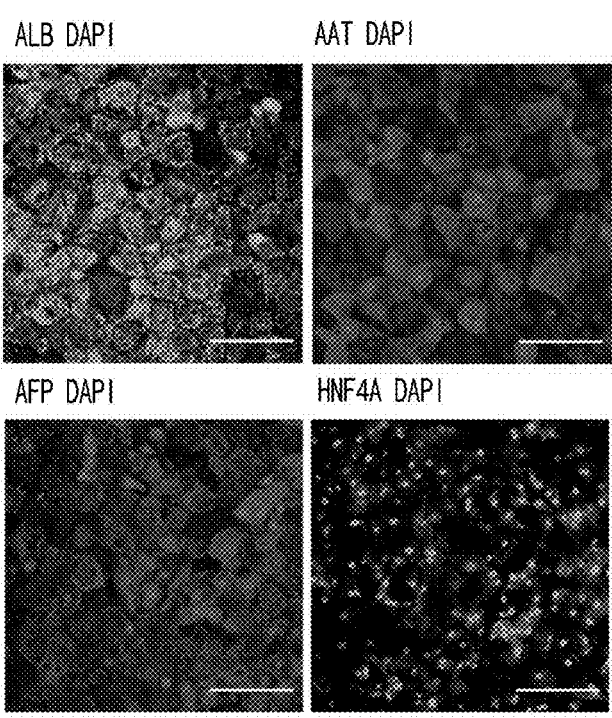
FIG. 4c is a diagram confirming the expression of hepatocyte-specific proteins such as ALB, AAT, AFP and HNF4A in the hepatocytes differentiated from the CYP1A1-mCherry hiPSC cell line by immunocytochemical analysis.

As a result of immunocytochemical analysis, as shown in FIG. 4c, the expression of hepatocyte-specific proteins such as ALB, AAT, AFP and HNF4A was confirmed in the differentiated hepatocytes (FIG. 4c).

Figure 4D:
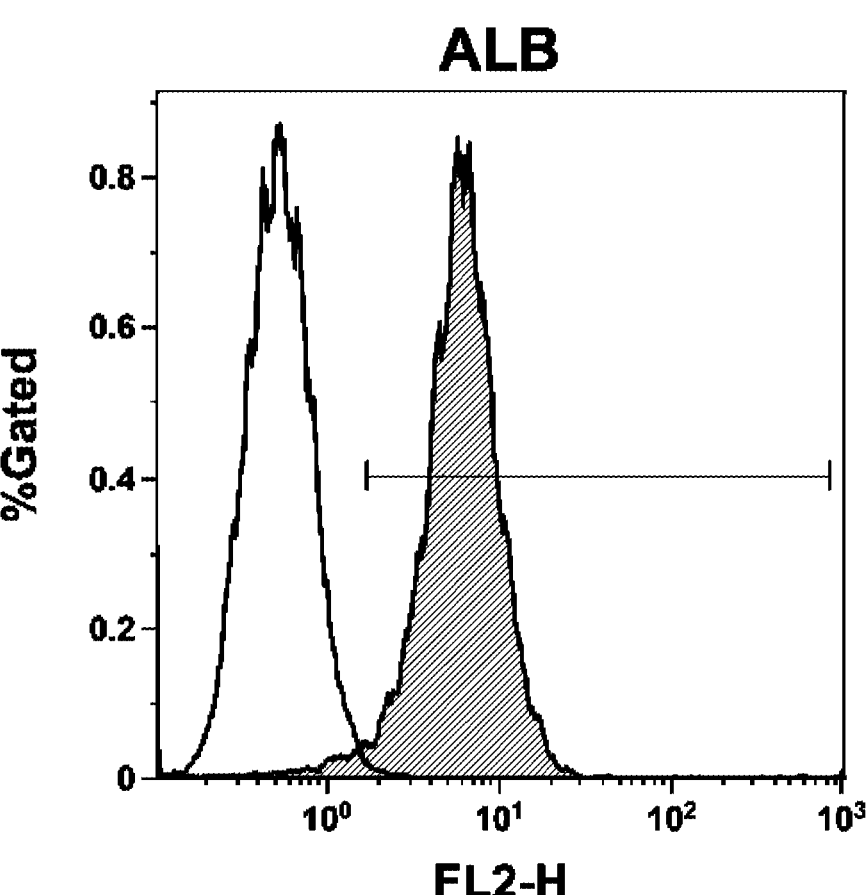
FIG. 4d is a diagram confirming the ratio of albumin-expressing cells by flow cytometry in the hepatocytes differentiated from the CYP1A1-mCherry hiPSC cell line.
Figure 4E:
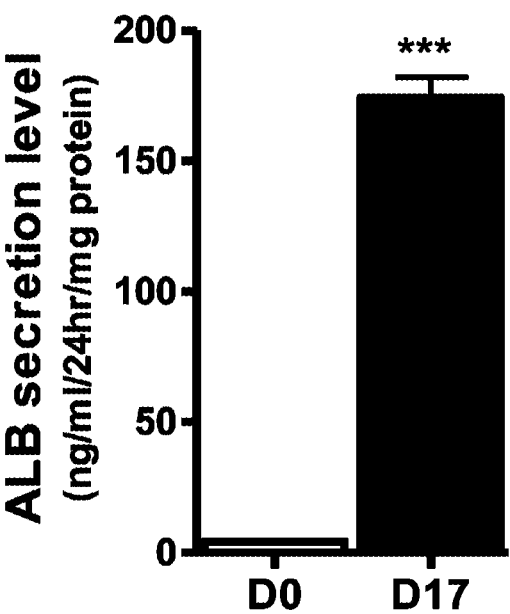
FIG. 4e is a diagram confirming the level of albumin secretion into plasma in the hepatocytes differentiated from the CYP1A1-mCherry hiPSC cell line.

In addition, the ratio of albumin-expressing cells was examined by the flow cytometry method of <Experimental methods>4, and it was confirmed that more than 96% of cells were albumin-positive HLCs on day 17 (FIG. 4d).

Figure 4F:
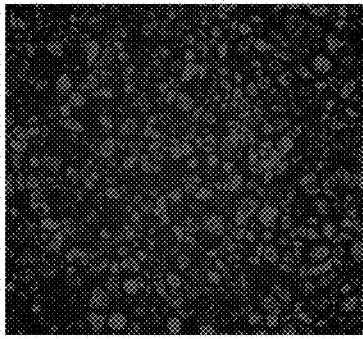
FIG. 4f is a diagram showing the results of low-density lipoprotein (LDL)-uptake analysis in the hepatocytes differentiated from the CYP1A1-mCherry hiPSC cell line.

The function of the differentiated HLCs was confirmed by detection of albumin secretion into plasma (FIG. 4e) and low-density lipoprotein (LDL)-absorption analysis (FIG. 4f).

Figure 4G:
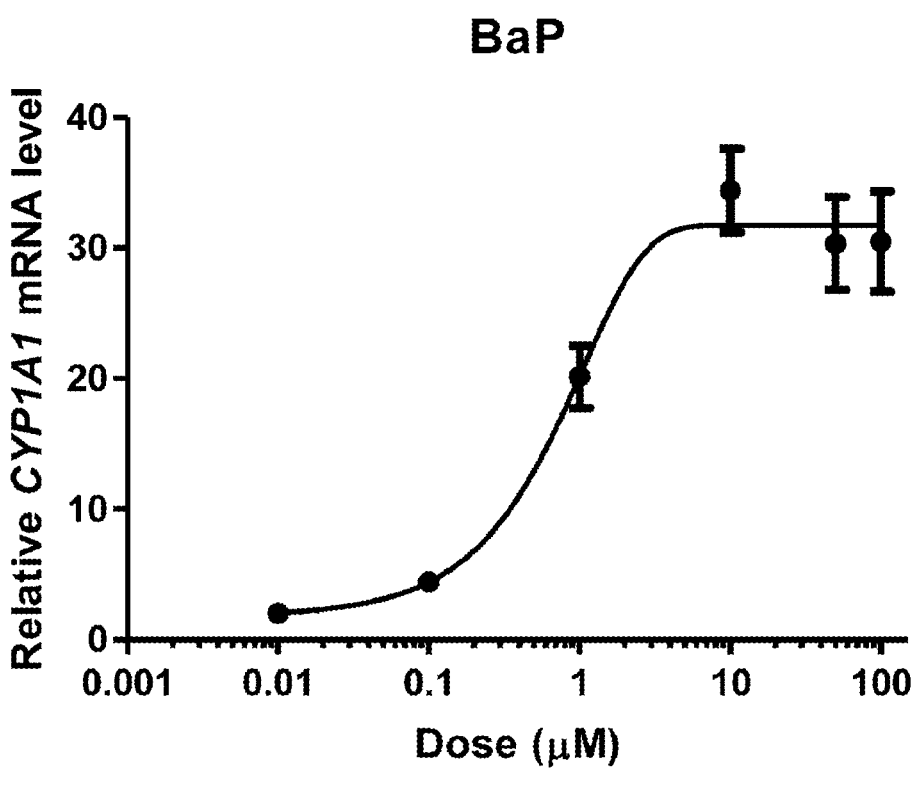
FIG. 4g is a diagram showing the dose-response curves of CYP1A1 inducers such as Bap and TCDD in the hepatocytes differentiated from the CYP1A1-mCherry hiPSC cell line.
Figure 4G:
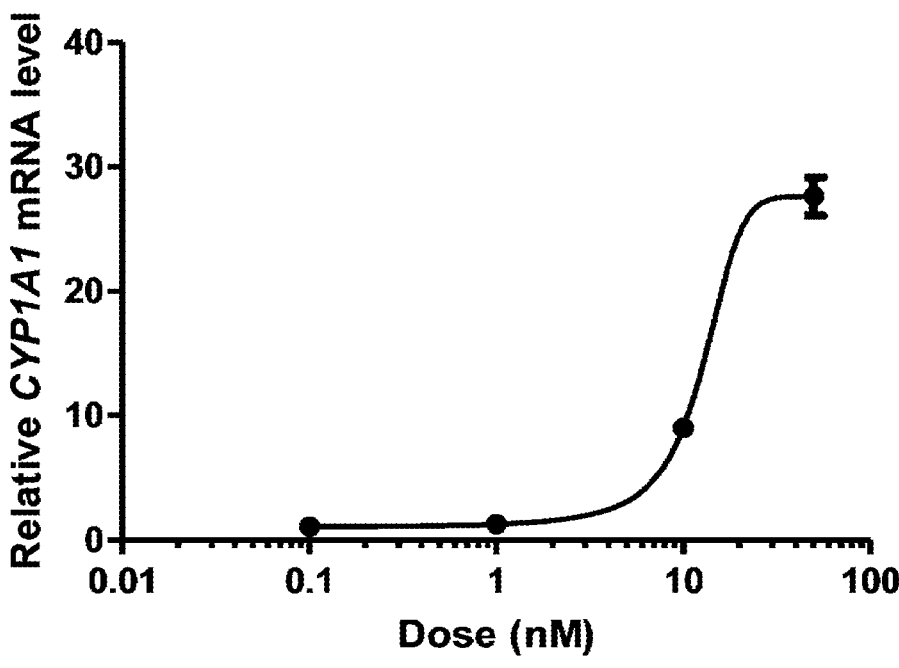

Dose-response curves of known CYP1A1 inducers (benzo [a] pyrene (BaP) and TCDD) indicate that the differentiated HLCs exhibit drug responses similar to those of other models by these chemicals (FIG. 4g).

From the above results, it was confirmed that the CYP1A1-mCherry hiPSC line successfully differentiated into HLCs by expressing essential liver markers and functions normally.

<Experimental Example 3> Confirmation of Expression of CYP1A1-mCherry Fusion Protein in Hepatocytes Differentiated from CYP1A1-mCherry hiPSCs Binding and expression of CYP1A1 and mCherry were confirmed in CYP1A1-mCherry HLCs.

Figure 5B:
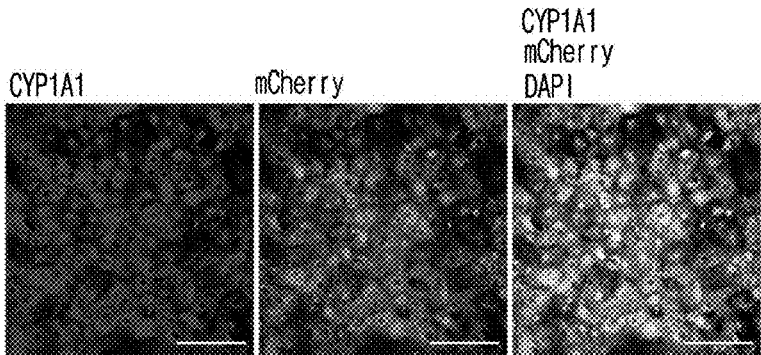
FIG. 5b is a diagram confirming the co-localization of CYP1A1 and mCherry on day 17 hepatocytes differentiated from the CYP1A1-mCherry hiPSC cell line in the absence of a CYP1A1 inducer (scale bar=200 μm).
Figure 5C:
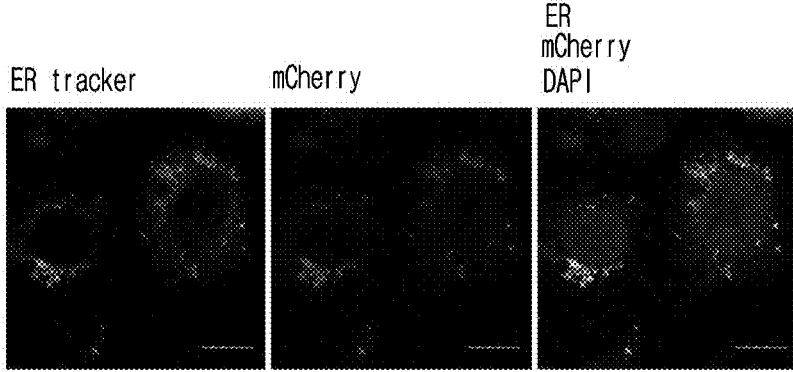
FIG. 5c is a diagram confirming that mCherry is expressed in the perinuclear endoplasmic reticulum (ER), which is a position where CYP1A1 is mainly present (scale bar=20 μm).

The expression levels of CYP1A1 and mCherry mRNAs was similar (FIG. 5a), and it was confirmed that CYP1A1 and mCherry were co-localized in HLCs differentiated from CYP1A1-mCherry hiPSCs on day 17 in the absence of a CYP1A1 inhibitor (FIG. 5b). In addition, it was confirmed that mCherry was expressed in the perinuclear endoplasmic reticulum (ER), where CYP1A1 is mainly present (FIG. 5c).

Next, to confirm whether mCherry signals could be induced by AHR agonists, differentiated CYP1A1-mCherry HLCs were treated with the known AHR agonists BaP and TCDD.

Figure 6A:
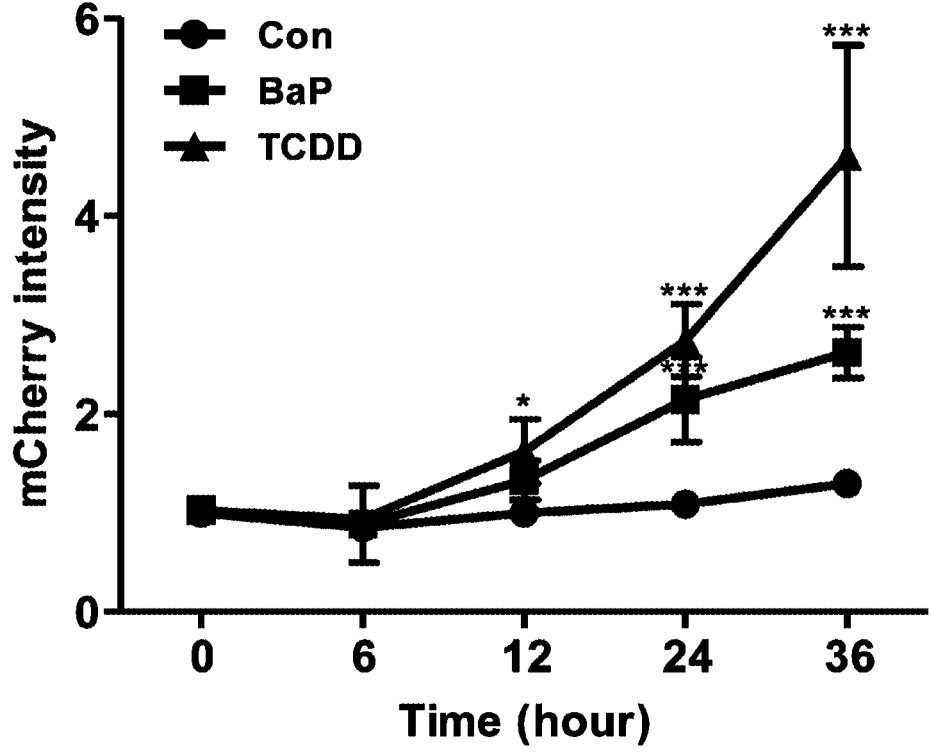
FIG. 6a is a diagram confirming the time-dependent increase in mCherry intensity after BaP and TCDD treatment in CYP1A1-mCherry HLC (N=4, * $p<0.05$, *** $p<0.001$).
Figure 6B:
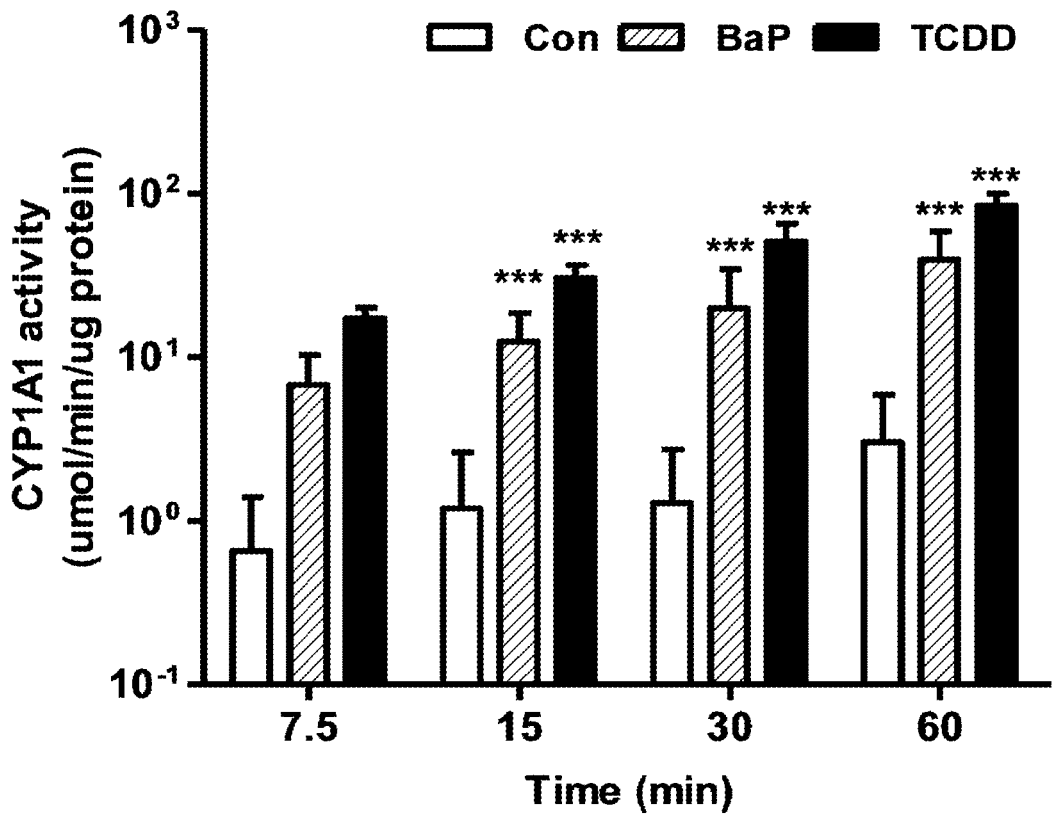
FIG. 6*b* is a diagram showing the CYP1A1 activity by treatment of AHR agonists such as BaP and TCDD in CYP1A1-mCherry HLC for 60 minutes (N=4. *** p<0.001).
Figure 6C:
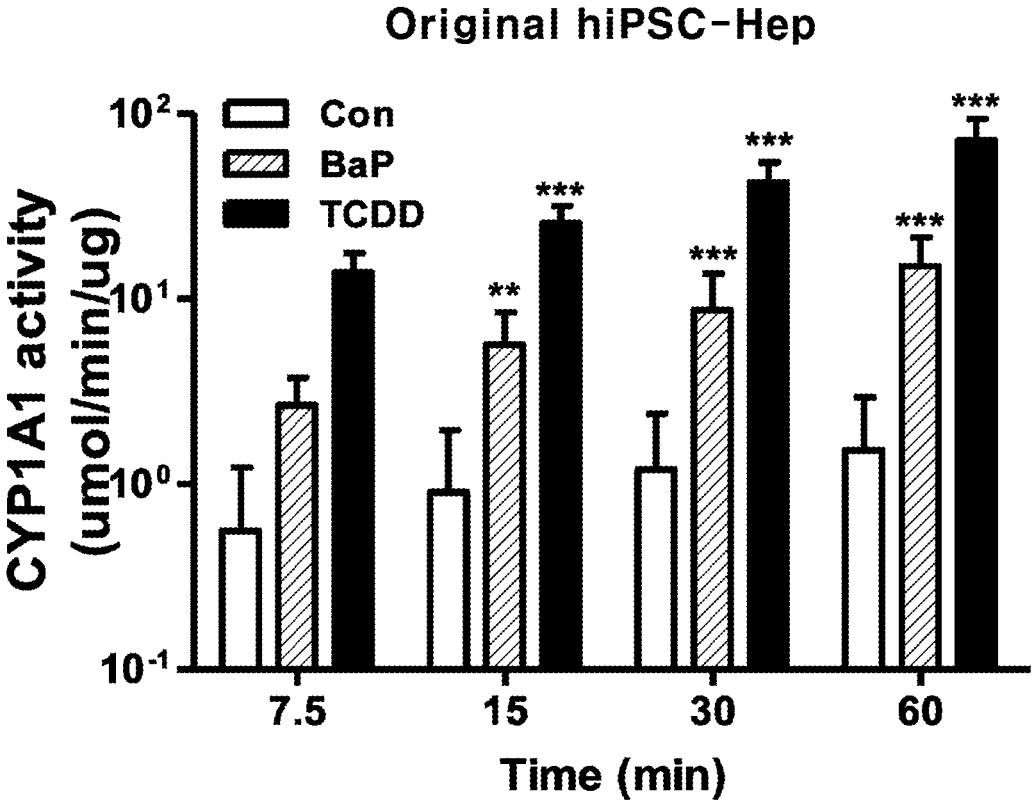
FIG. 6*c* is a diagram confirming the CYP1A1 activity by treatment of AHR agonists such as BaP and TCDD for 60 minutes in HLC derived from hiPSC without introduction of the control CYP1A1-mCherry (N=4. *** p<0.001).

As a result, it was confirmed that the intensity of mCherry was increased in HLC when treated with an AHR agonist (FIG. 6a). In addition, CYP1A1 activity was increased in BaP- and TCDD-treated CYP1A1-mCherry HLCs (FIG. 6b), which was confirmed to be similar to the control hiPSC-derived HLCs (FIG. 6c).

To confirm whether the induction of CYP1A1 was mediated by AHR, CYP1A1-mCherry HLCs were treated with BaP and TCDD in combination with the AHR antagonist CH223191.

Figure 7A:
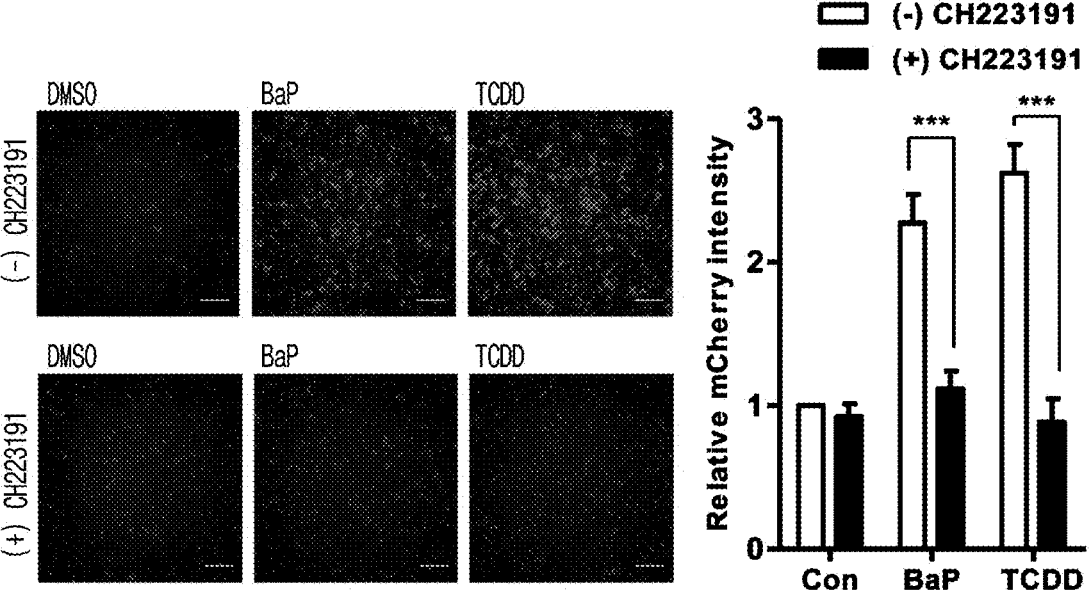
FIG. 7*a* is a diagram showing the results of analyzing mCherry expression by HCS imaging (left) and intensity quantification (right) after co-treating AHR agonists (BaP and TCDD) and antagonists (CH223191) on CYP1A1-mCherry HLC (N=4, *** p<0.001, scale bar=200 μm).
Figure 7B:
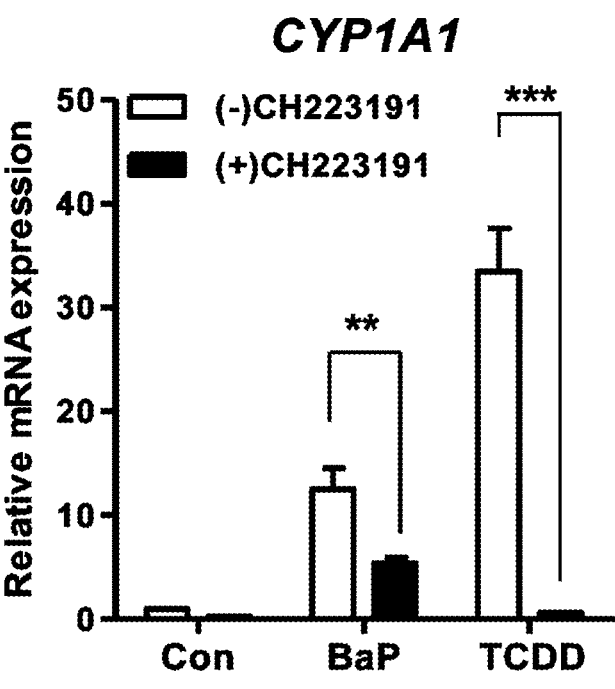
FIG. 7*b* is a diagram confirming the expression of CYP1A1 and mCherry mRNAs after co-treating AHR agonists (BaP and TCDD) and antagonists (CH223191) on CYP1A1-mCherry HLC (N=3,  p<0.01, * p<0.001).
Figure 7B:
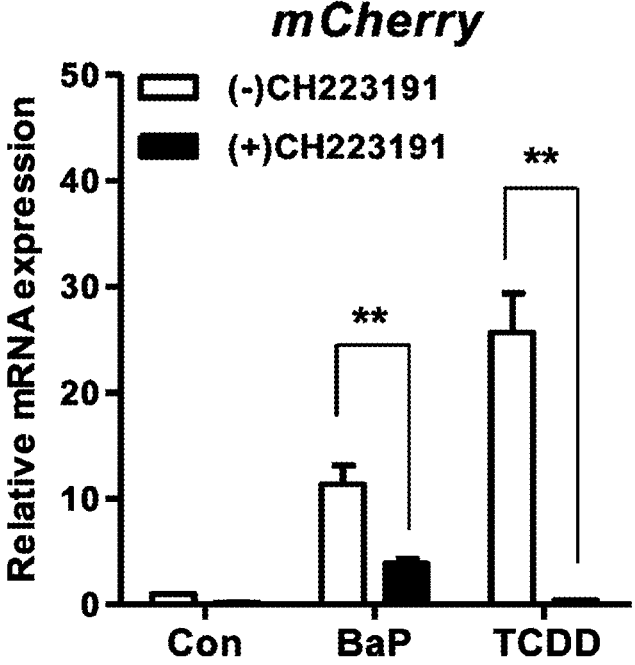
Figure 7C:
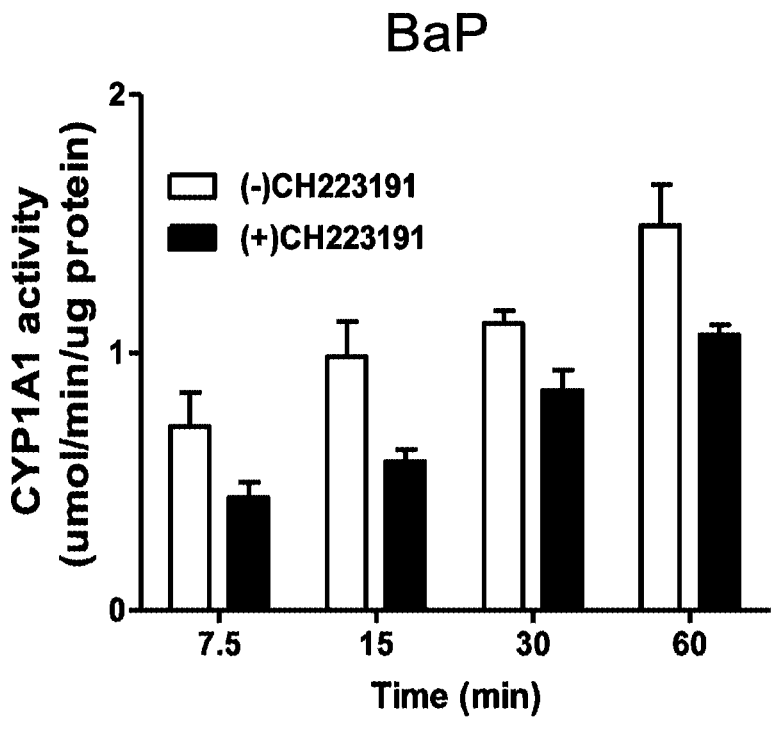
FIG. 7*c* is a diagram confirming the changes in activity of CYP1A1 after co-treating AHR agonists (BaP and TCDD) and antagonists (CH223191) on CYP1A1-mCherry HLC (N=2).
Figure 7C:
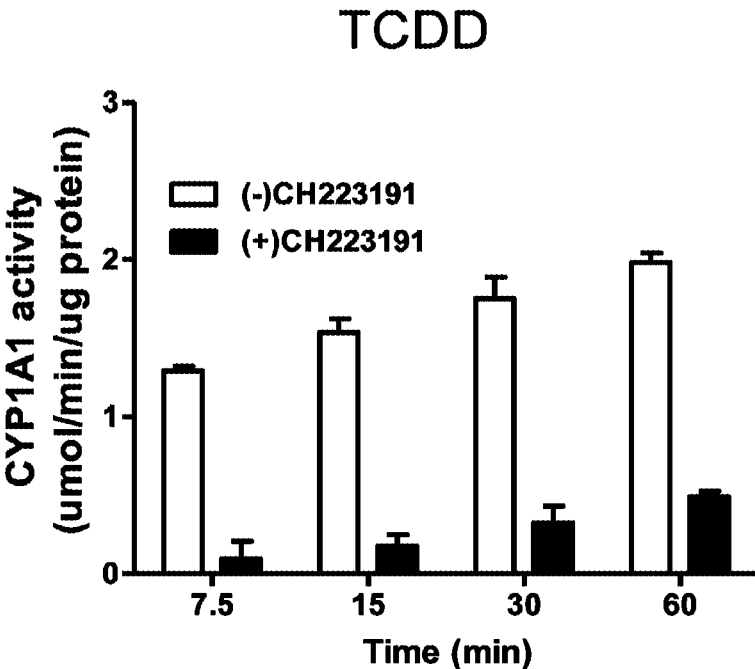

As a result, it was confirmed that CH223191 significantly suppressed the intensity of mCherry in both the BaP- and TCDD-treated groups (FIG. 7a). The transcript expression levels of CYP1A1 and mCherry were reduced by the treatment of CH223191 (FIG. 7b). In addition, the co-treatment of CH223191 and BaP or TCDD reduced the activity of CYP1A1 (FIG. 7c).

These results indicate that the CYP1A1-mCherry hiPSC-derived HLCs of the present invention can be used for drug testing of the AHR-CYP1A1 axis.

Figure 8A:
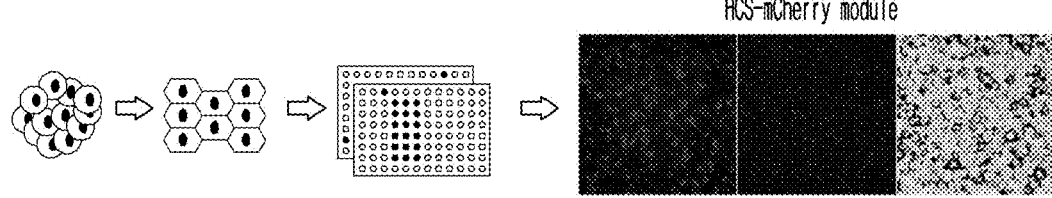
FIG. 8*a* is a schematic diagram showing the flow of a screening system based on HCS (High-Content Screening) and CYP1A1-mCherry hiPSC.
Figure 8B:
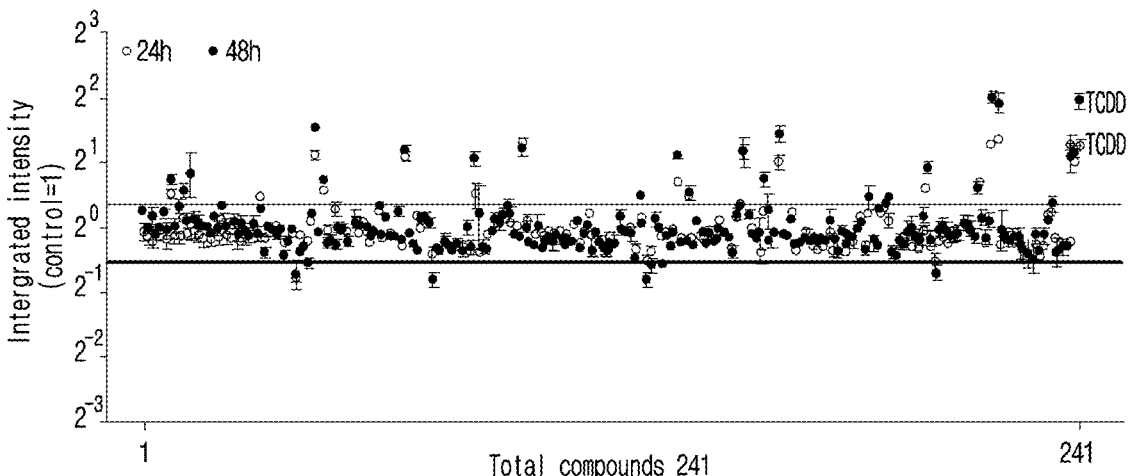
FIG. 8*b* is a diagram showing the results of screening with 241 chemicals from a commercially available library in CYP1A1-mCherry HLC treated for 24 hours or 48 hours. The two horizontal lines represent cutoff thresholds for hit selection (up or down 30% compared to the non-treated control, N=6).

<Experimental Example 4> Hepatotoxic Chemical Screening Using CYP1A1-mCherry HLCs An automated analysis protocol using a HCS (High-Content Screening) device was set up for screening (FIG. 8a). Using this module, a total of 241 chemicals were screened, including commercial libraries for hepatotoxic formulations (210 compounds) and nuclear receptor modulators (29 compounds) as well as BaP and TCDD as positive controls in the CYP1A1-mCherry HLCs treated for 24 or 48 hours (FIG. 8b).

4-1. Selection of Compounds that Increase mCherry Expression

Figure 9A:
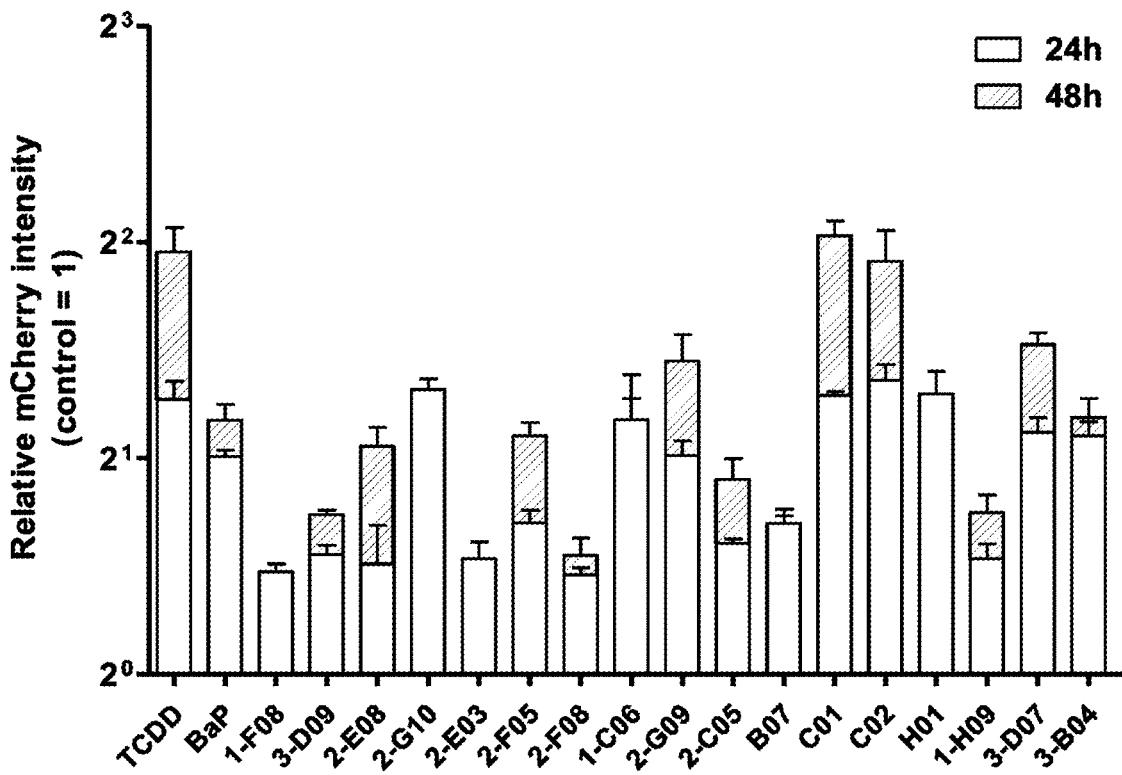
FIG. 9*a* is a diagram showing the mCherry intensity of 17 selected chemicals that increase the mCherry intensity by 30% or more in CYP1A1-mCherry HLC treated for 24 hours or 48 hours (N=6).

As a result of screening compounds that increase mCherry expression, 17 compounds that increase mCherry intensity by 30% or more compared to the untreated control group were selected (FIG. 9a). Among them, 10 compounds were known as drugs that directly or indirectly induce CYP1A1 or AHR, and the other 7 compounds were not known as potential activators of AHR or CYP1A1 until now.

Figure 9B:
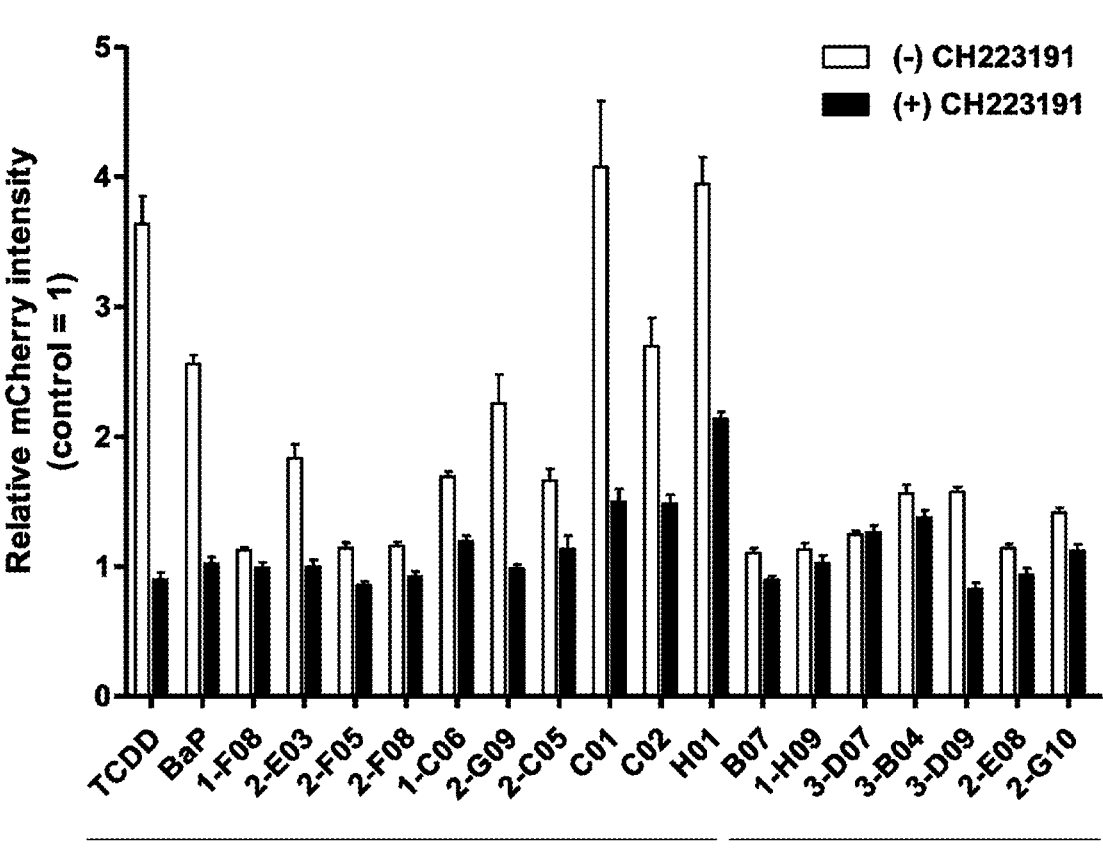
FIG. 9*b* is a diagram showing the results of measuring the mCherry intensity after co-treating 17 compounds and an AHR antagonist (CH223191) in combination (N=6).

Even though cell death was not detectable with the naked eye, the detected upregulation of mCherry signal intensity could be autofluorescence caused by cell death or other reasons. Therefore, the mCherry activity was measured by co-treating 17 types of compounds, CYP1A1-regulators and AHR antagonists. It was confirmed that the co-treatment of most CYP1A1-modulators and CH223191, an AHR antagonist, reduced mCherry intensity in CYP1A1-mCherry HLCs (FIG. 9b).

Figure 9C:
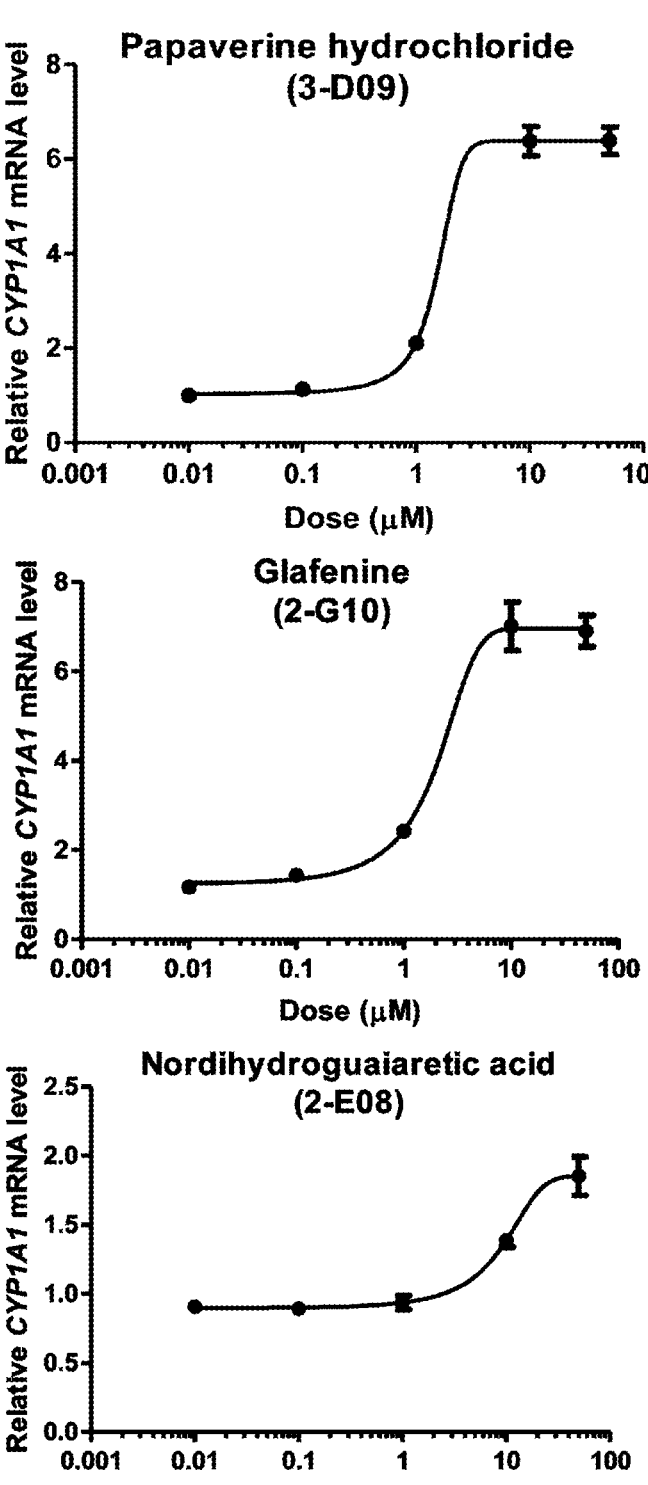
FIG. 9*c* is a diagram showing the dose-response curves for papaverine hydrochloride, nordihydroguaiaretic acid and glafenine.

Among the identified AHR modulator candidates, papaverine hydrochloride, nordihydroguaiaretic acid and glafenine showed significant differences in terms of mCherry intensity by CH223191 exposure. The effects of these chemicals were confirmed according to the dose (FIG. 9c). Papaverine hydrochloride and glafenine showed a 6- to 7-fold increase and maximal induction at the concentrations used for screening. Nordihydroguaiaretic acid exhibited a lower effect (~2 times) than the other two chemicals.

From the above results, the present inventors selected three new AHR agonists that inhibit the expression of AHR by mCherry-based HCS.

4-2. Selection of Compounds that Reduce mCherry Expression

Figure 10A:
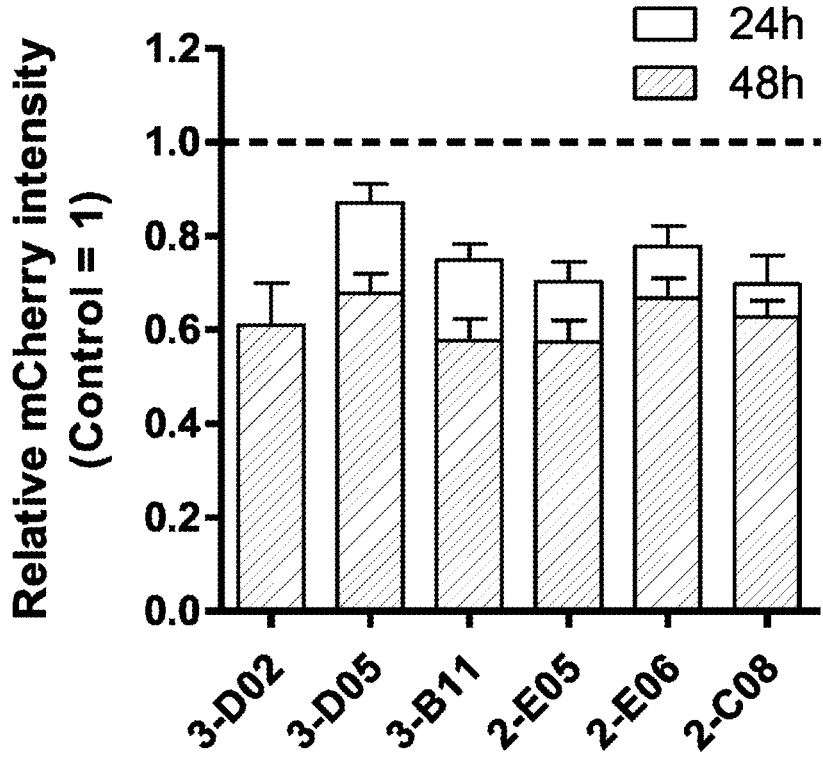
FIG. 10*a* is a diagram showing the mCherry intensity of 6 selected chemicals that lowered the mCherry intensity by 70% or more in CYP1A1-mCherry HLC treated for 24 hours or 48 hours (N=6, dotted line indicates untreated control level).
Figure 10B:
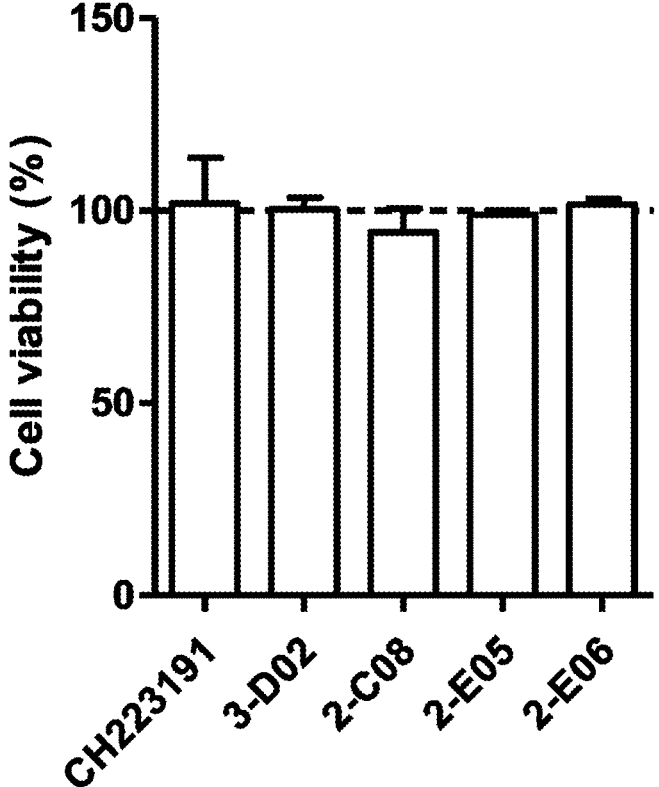
FIG. 10*b* is a diagram showing the results of measuring the cell viability of CYP1A1-mCherry HLC treated with CYP1A1 down-regulators such as 3-D02, 2-008, 2-E05 and 2-E06 selected from the screening (N=3).

As a result of screening chemicals that reduce mCherry expression, first, six chemicals that lower mCherry intensity by more than 70% compared to the untreated control were selected (FIG. 10a). None of these chemicals have been reported as AHR antagonists or CYP1A1 inhibitors.

In order to verify whether the decrease of CYP1A1 was due to the hepatotoxicity of the chemical, cell viability was confirmed by the method described in <Experimental Methods>11 after treatment of the compound. As a result, none of these compounds induced cell death at the working concentration (10 μM).

Figure 10C:
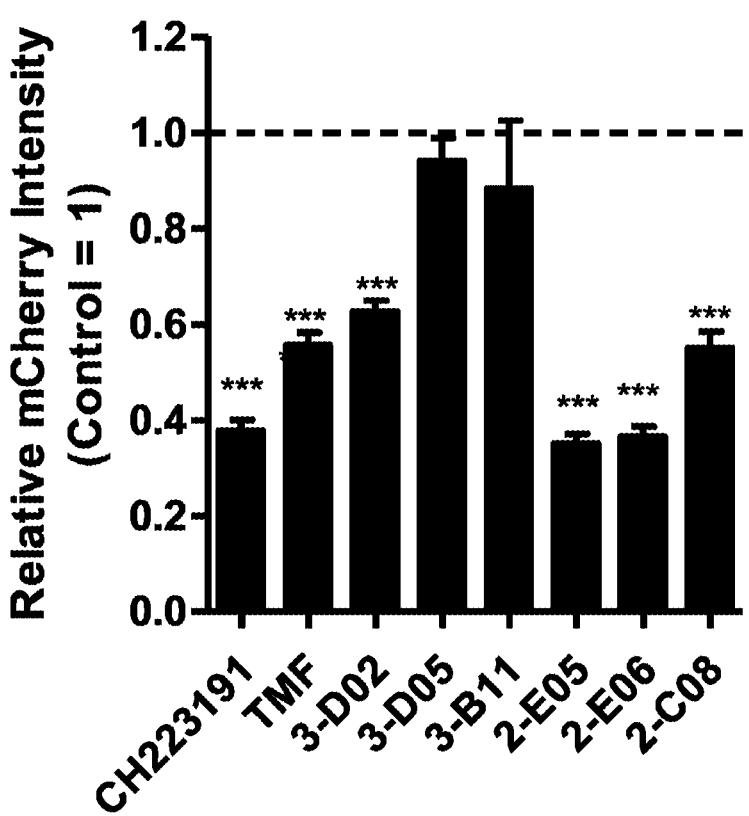
FIG. 10*c* is a diagram showing the changes in mCherry intensity caused by treating six CYP1A1 down-regulators selected as a result of treating known AHR antagonists (CH223191 and TMF) on CYP1A1-mCherry HLC and screening (N=6).
Figure 10D:
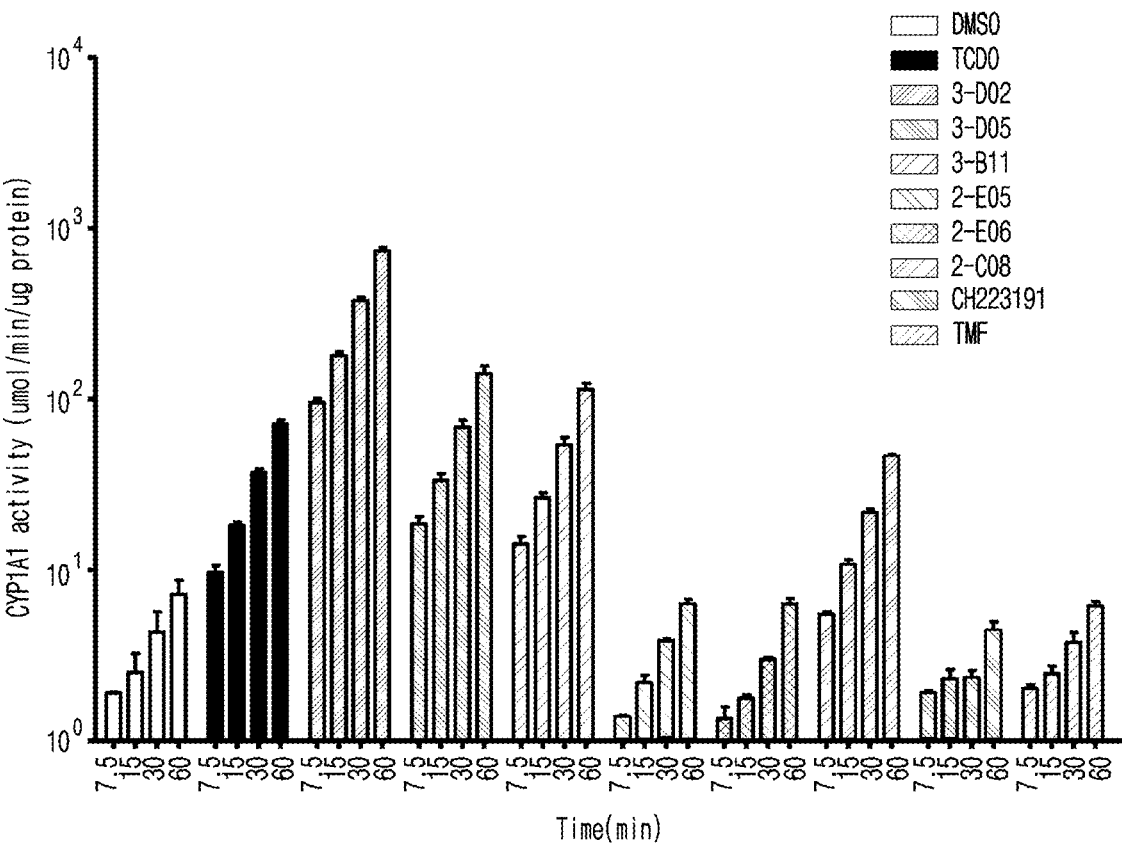
FIG. 10*d* is a diagram comparing the amount of decrease in CYP1A1 activity between six CYP1A1 down-regulators selected as a result of screening and previously known substances that reduce the expression of CYP1A1 (CH223191 and TMF).
Figure 10E:
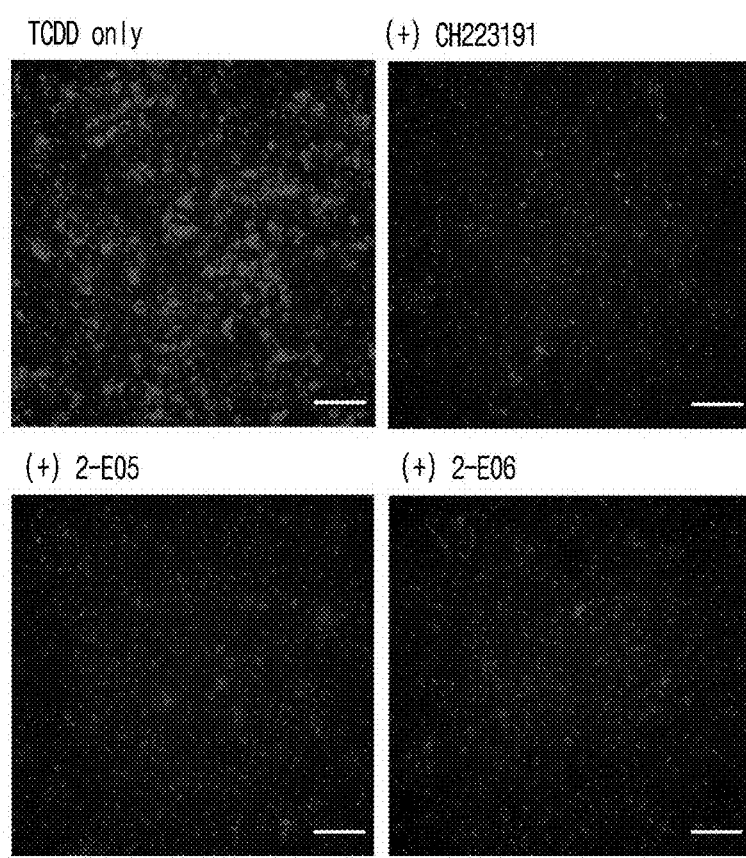
FIG. 10*e* is a diagram confirming the effect of inhibiting the expression of mCherry induced by TCDD by CH223191, 2-E05 and 2-E06 (scale bar=200 μm).

The inhibitory effects of known AHR antagonists on TCDD, 3-D02, 2-E05, 2-E06 and 2-008 were compared. As a result, they showed a significant decrease of mCherry intensity compared to CH223191 and TMF (FIG. 10c). In particular, it was confirmed that 2-E05 (yangonin) and 2-E06 (desmethoxyyangonin) inhibited the effect of TCDD on CYP1A1 activity and mCherry expression at the levels of the non-treated control and CH223191 without cell death in CYP1A1-mCherry HLCs (FIGS. 10d and 10e).

Figure 10F:
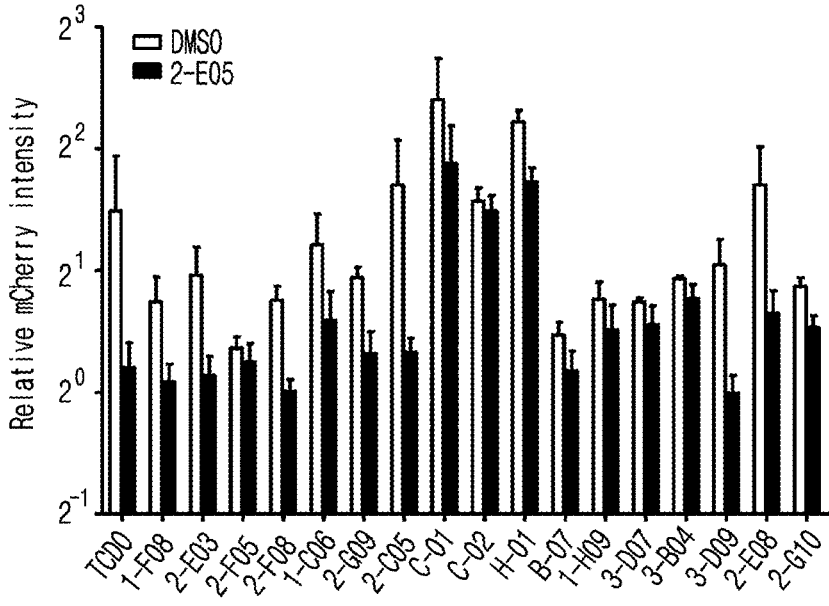
FIG. 10*f* is a diagram confirming the CYP1A1 expression level when 17 types of CYP1A1 expression increasing substances and 2-E05 were treated in combination.

As a result of the combined treatment of the 17 CYP1A1 expression increasing substances identified in <Experimental Example 4-1> and the above two chemicals, it was confirmed that the level of CYP1A1 expression was reduced (FIG. 10f). In addition, comparison with CH223191 and TMF showed equivalent ability to inhibit the upregulation effect of TCDD and other upregulators identified by the screening.

Through the above results, it was possible to screen a new chemical that regulates the expression of CYP1A1 using the CYP1A1-mCherry hiPSC line, and the usefulness of the selected compound was proved by the HCS system.

<Experimental Example 5> Comparison of CYP1A1-mCherry HLCs and hPH and HepG2 Cell Lines Despite the advantages of live screening, the immaturity of hiPSC-derived HLCs can present problems for the reliability of the hepatotoxicity test results. Therefore, the present inventors compared hiPSC-HLCs with hPH and HepG2 cells most commonly used in hepatotoxicity tests. To investigate the cellular similarity between them, the transcriptional profiles of hiPSC-derived HLCs, hPH and HepG2 cells with or without BaP treatment were analyzed by microarrays.

Figure 11:
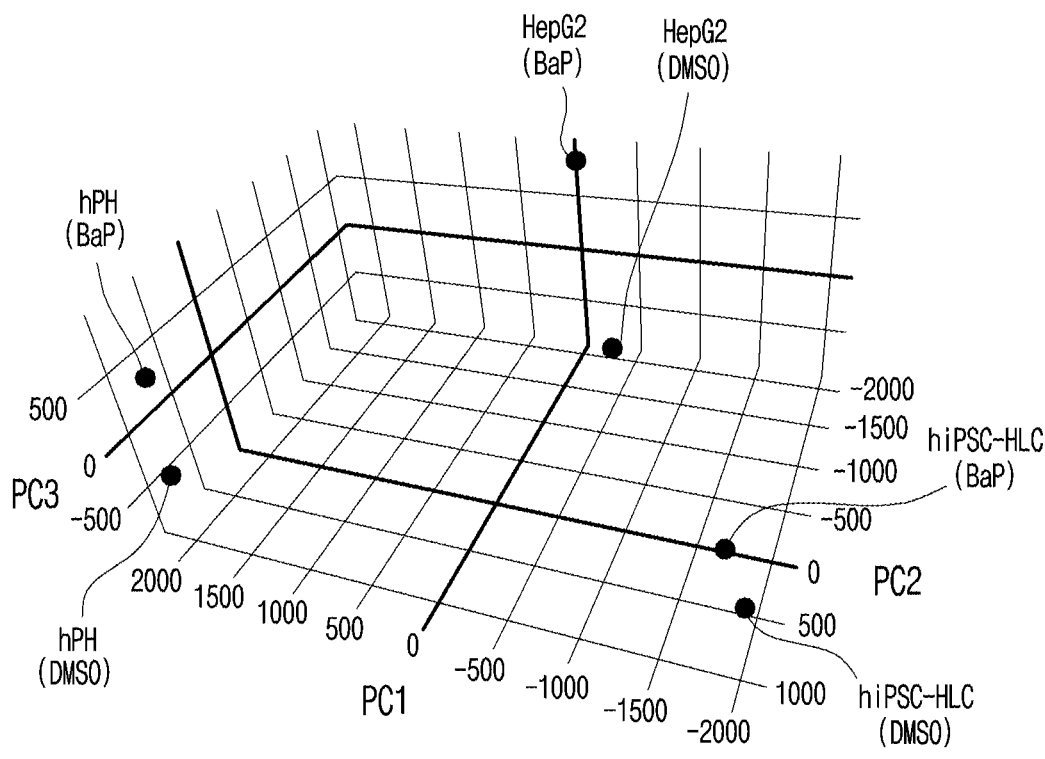
FIG. 11 is a diagram showing the results of analyzing hiPSC-HLC, hPH and HepG2 cells by principal component analysis.

As a result, as shown in FIG. 11, In principle component analysis (PCA), the three cell types showed overall distinct cellular characteristics and were grouped by cell type rather than treatment group. The principal components (PC) 1 and 2 contained the genes involved in general cellular processes, whereas the principal component (PC) 3 contained the genes related to drug metabolism in the three cell types (FIG. 11).

Figure 12A:
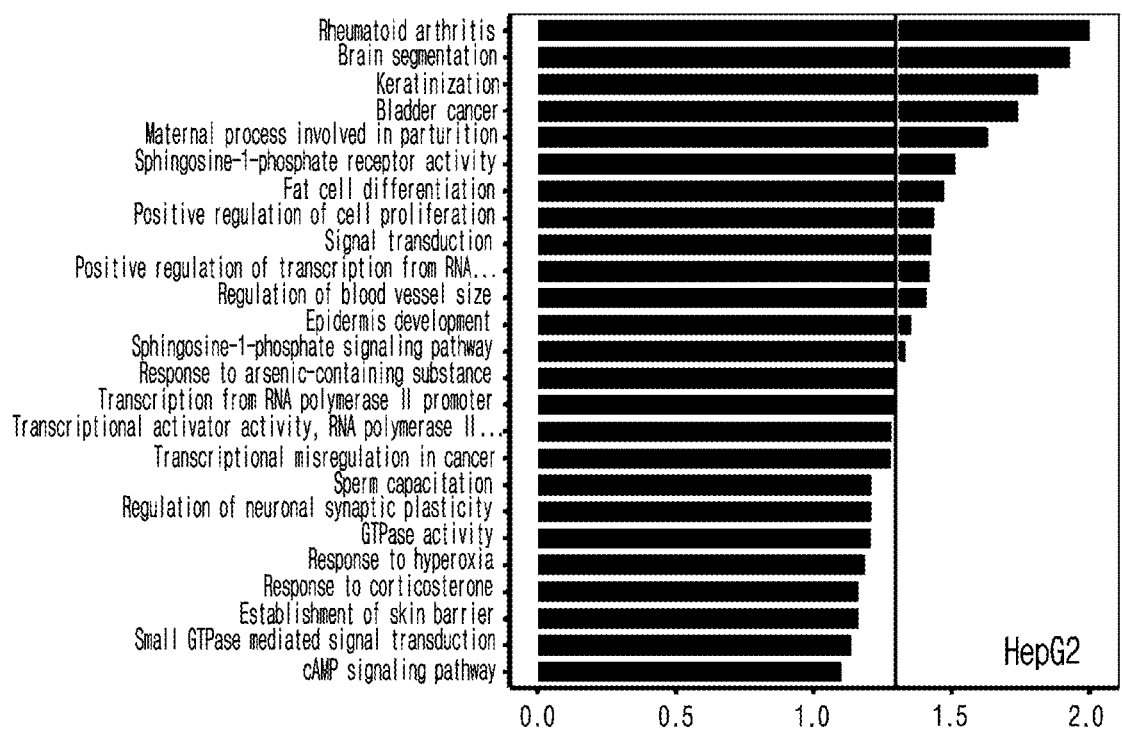
FIG. 12 is a diagram showing the top 25 functional annotations of hiPSC-HLC(a), hPH(b) and HepG2(c) through gene ontology and KEGG-path analysis, wherein red asterisks indicate drug metabolism and BaP-related terms (vertical gray line indicates p-value=0.05).
Figure 12B:
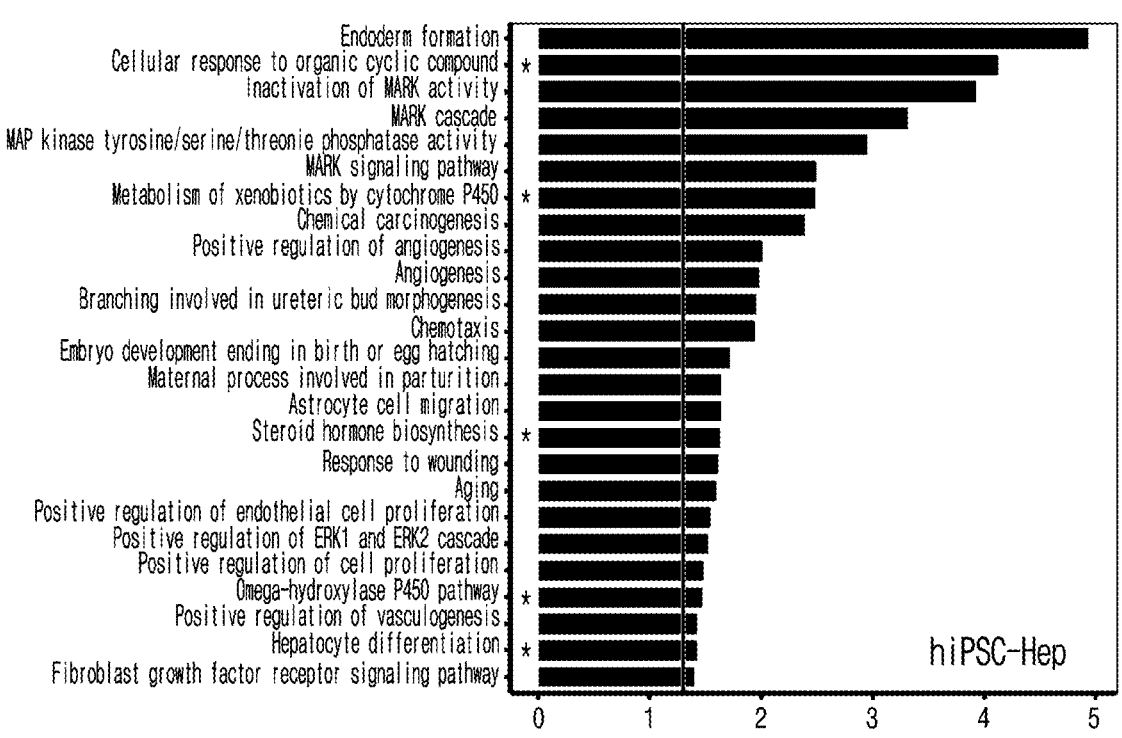
Figure 12C:
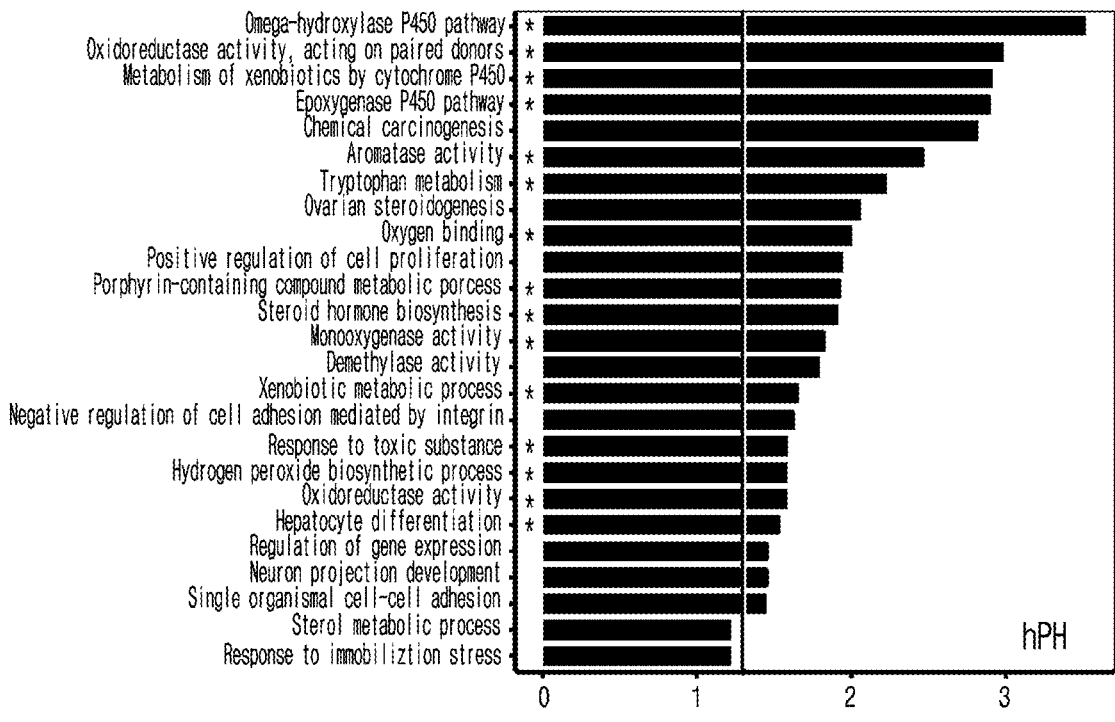
Figure 13A:
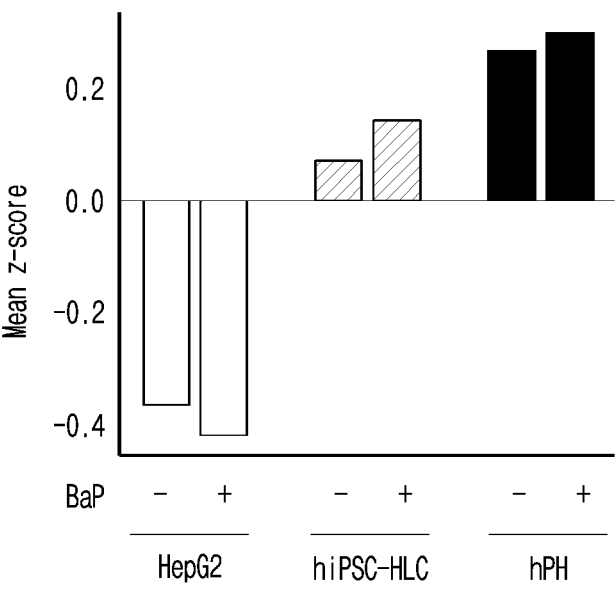
FIG. 13*a* is a diagram showing the mean z-score of genes in a KEGG pathway: hsa00980. BaP treatment increased related gene expression in hiPSC-HLC and hPH, and decreased equally in HepG2 cells.
Figure 13B:
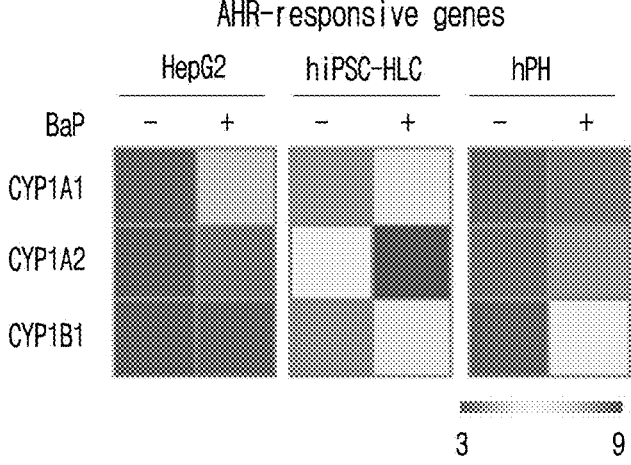
FIG. 13*b* is a diagram showing the heat map for AHR-responsive gene induction by BaP treatment in HepG2, hiPSC-HLC and hPH. BaP treatment increased all AHR-responsive genes in hiPSC-HLC and hPH.

As a result of functional annotation analysis and KEGG pathway investigation based on gene ontology including the top 100 genes upregulated by BaP treatment, the terms related to drug metabolism enzymes were increased in hiPSC-HLCs and hPH, whereas the terms related to drug metabolism were not increased in HepG2 cells (p<0.05) (FIGS. 12a to 12c). The genes involved in xenobiotic metabolism by cytochrome P450 (KEGG-pathway: hsa00980) were highly expressed and responsive to BaP treatment in hiPSC-HLCs and hPH. However, these genes showed reduced expression after the treatment of BaP in HepG2 cells (FIG. 13a). In particular, all AHR-responsive genes (CYP1A1, CYP1A2 and CYP1B1) were enhanced by the treatment of BaP in hiPSC-HLCs and hPH, while CYP1A2 and CYP1B1 were not induced by the treatment of BaP in HepG2 cells (FIG. 13b).

These results indicate that hiPSC-HLCs are much closer to hPH and represent a better cell model for drug metabolism and toxicity tests than HepG2 cells.

What is claimed is:

1. A human induced pluripotent stem cell (hiPSC) line for screening an AHR (aryl hydrocarbon receptor) modulator, the cell line expressing a fluorescent protein-tagged CYP1A1 protein, wherein the fluorescent-tagged CYP1A1 protein is produced by CRISPR-Cas9-mediated knock-in at the CYP1A1 locus using:

(i) a single guide RNA selected from SEQ ID NOs: 1-3; and (ii) a targeting vector comprising a fluorescent protein insertion cassette, the cell line having been deposited under the accession number KCTC 14186BP.

2. The human induced pluripotent stem cell line for screening an AHR modulator according to claim 1, wherein the fluorescent protein is selected from the group consisting of green fluorescence protein (GFP), cyan fluorescence protein (CFP), yellow fluorescence protein (YFP) and red fluorescence protein (RFPD).

3. The human induced pluripotent stem cell line for screening an AHR modulator according to claim 1, wherein the fluorescent protein is mCherry.

4. The human induced pluripotent stem cell line for screening an AHR modulator according to claim 1, wherein the human induced pluripotent stem cell line is prepared by transfection using pMCDT-A vector as a targeting vector.

5. The human induced pluripotent stem cell line for screening an AHR modulator according to claim 1, wherein the human induced pluripotent stem cell line expresses the markers NANOG, OCT4, SOX2, TRA-1-60 and TRA-1-81.

6. The human induced pluripotent stem cell line for screening an AHR modulator according to claim 1, wherein the human induced pluripotent stem cell line expresses Pax6, Otx2, alpha-SMA, EOMES, Brachyury, FOXA2, GATA4 and Sox17 upon differentiation into three germ layers.

7. An AHR modulator screening method comprising the following steps:

1) contacting a test substance to the human induced pluripotent stem cell line (hiPSC line) of claim 1;

2) measuring the signal intensity of the fluorescent protein in the human induced pluripotent stem cell line contacted with the test substance; and 3) selecting a test substance that changes the signal intensity of the fluorescent protein compared to a control sample.

8. The AHR modulator screening method according to claim 7, wherein the control sample of step 3) is BaP or TCDD.

9. An AHR modulator screening method according to claim 7, wherein the screening method is performed by a high content screening (HCS) system.

10. The AHR modulator screening method according to claim 7, wherein the screening method is performed while the cells are alive.

11. The AHR modulator screening method according to claim 7, wherein the AHR modulator is at least one selected from the group consisting of papaverine hydrochloride, nordihydroguaiaretic acid, glafenine, yangonin and desmethoxyyangonin.

* * * * *

SEQUENCE LISTING

<160> NUMBER OF SEQ ID NOS: 39

<210> SEQ ID NO 1
<211> LENGTH: 23
<212> TYPE: DNA
<213> ORGANISM: Artificial Sequence
<220> FEATURE:
<223> OTHER INFORMATION: single guide RNA 1

<400> SEQUENCE: 1
gcattgatcc tcctgtccat ggg                                              23

<210> SEQ ID NO 2
<211> LENGTH: 23
<212> TYPE: DNA
<213> ORGANISM: Artificial Sequence
<220> FEATURE:
<223> OTHER INFORMATION: single guide RNA 4

<400> SEQUENCE: 2
taggtagtgg ctcccttcaa agg                                              23

<210> SEQ ID NO 3
<211> LENGTH: 23
<212> TYPE: DNA
<213> ORGANISM: Artificial Sequence
<220> FEATURE:
<223> OTHER INFORMATION: single guide RNA 5

<400> SEQUENCE: 3
ctggcactga cccctttgaa ggg                                              23

<210> SEQ ID NO 4
<211> LENGTH: 20
<212> TYPE: DNA
<213> ORGANISM: Artificial Sequence
<220> FEATURE:
<223> OTHER INFORMATION: CYP1A1 forward

<400> SEQUENCE: 4
aggcttttac atccccaagg                                                  20

<210> SEQ ID NO 5
<211> LENGTH: 20
<212> TYPE: DNA
<213> ORGANISM: Artificial Sequence
<220> FEATURE:
<223> OTHER INFORMATION: CYP1A1 reverse

<400> SEQUENCE: 5
ttgtcgatag caccatcagg                                                  20

<210> SEQ ID NO 6
<211> LENGTH: 21
<212> TYPE: DNA
<213> ORGANISM: Artificial Sequence
<220> FEATURE:
<223> OTHER INFORMATION: mCherry forward

<400> SEQUENCE: 6
gtgagcactt ccaaatgcag c                                                21

<210> SEQ ID NO 7
<211> LENGTH: 21
<212> TYPE: DNA
<213> ORGANISM: Artificial Sequence -continued

```
<220> FEATURE:
<223> OTHER INFORMATION: mCherry reverse

<400> SEQUENCE: 7
ccttgaagcg catgaactcc t                                           21

<210> SEQ ID NO 8
<211> LENGTH: 20
<212> TYPE: DNA
<213> ORGANISM: Artificial Sequence
<220> FEATURE:
<223> OTHER INFORMATION: PAX6 forward

<400> SEQUENCE: 8
gtgtccaacg gatgtgtgag                                             20

<210> SEQ ID NO 9
<211> LENGTH: 20
<212> TYPE: DNA
<213> ORGANISM: Artificial Sequence
<220> FEATURE:
<223> OTHER INFORMATION: PAX6 reverse

<400> SEQUENCE: 9
ctagccaggt tgcgaagaac                                             20

<210> SEQ ID NO 10
<211> LENGTH: 20
<212> TYPE: DNA
<213> ORGANISM: Artificial Sequence
<220> FEATURE:
<223> OTHER INFORMATION: OTX2 forward

<400> SEQUENCE: 10
tgcaggggtt cttctgtgat                                             20

<210> SEQ ID NO 11
<211> LENGTH: 20
<212> TYPE: DNA
<213> ORGANISM: Artificial Sequence
<220> FEATURE:
<223> OTHER INFORMATION: OTX2 reverse

<400> SEQUENCE: 11
agggtcagag caattgacca                                             20

<210> SEQ ID NO 12
<211> LENGTH: 21
<212> TYPE: DNA
<213> ORGANISM: Artificial Sequence
<220> FEATURE:
<223> OTHER INFORMATION: alpha SMA forward

<400> SEQUENCE: 12
tgctctgggt tcgtcagagt c                                           21

<210> SEQ ID NO 13
<211> LENGTH: 20
<212> TYPE: DNA
<213> ORGANISM: Artificial Sequence
<220> FEATURE:
<223> OTHER INFORMATION: alpha SMA reverse

<400> SEQUENCE: 13
caggcaagtc actgtgtggc                                             20
```

```
<210> SEQ ID NO 14
<211> LENGTH: 21
<212> TYPE: DNA
<213> ORGANISM: Artificial Sequence
<220> FEATURE:
<223> OTHER INFORMATION: EOMES forward

<400> SEQUENCE: 14
aggcgcaaat aacaacaaca c                                            21

<210> SEQ ID NO 15
<211> LENGTH: 21
<212> TYPE: DNA
<213> ORGANISM: Artificial Sequence
<220> FEATURE:
<223> OTHER INFORMATION: EOMES reverse

<400> SEQUENCE: 15
attcaagtcc tccacgccat c                                            21

<210> SEQ ID NO 16
<211> LENGTH: 20
<212> TYPE: DNA
<213> ORGANISM: Artificial Sequence
<220> FEATURE:
<223> OTHER INFORMATION: Brachyury forward

<400> SEQUENCE: 16
gcgggaaaga gcctgcagta                                              20

<210> SEQ ID NO 17
<211> LENGTH: 20
<212> TYPE: DNA
<213> ORGANISM: Artificial Sequence
<220> FEATURE:
<223> OTHER INFORMATION: Brachyury reverse

<400> SEQUENCE: 17
ttccccgttc acgtacttcc                                              20

<210> SEQ ID NO 18
<211> LENGTH: 20
<212> TYPE: DNA
<213> ORGANISM: Artificial Sequence
<220> FEATURE:
<223> OTHER INFORMATION: FOXA2 forward

<400> SEQUENCE: 18
atgcactcgg cttccagtat                                              20

<210> SEQ ID NO 19
<211> LENGTH: 20
<212> TYPE: DNA
<213> ORGANISM: Artificial Sequence
<220> FEATURE:
<223> OTHER INFORMATION: FOXA2 reverse

<400> SEQUENCE: 19
cacgtacgac gacatgttca                                              20

<210> SEQ ID NO 20
<211> LENGTH: 20
<212> TYPE: DNA
<213> ORGANISM: Artificial Sequence
<220> FEATURE:
<223> OTHER INFORMATION: GATA4 forward
```

-continued

<400> SEQUENCE: 20
tccaaaccag aaaacggaag                                           20

<210> SEQ ID NO 21
<211> LENGTH: 20
<212> TYPE: DNA
<213> ORGANISM: Artificial Sequence
<220> FEATURE:
<223> OTHER INFORMATION: GATA4 reverse

<400> SEQUENCE: 21
ctgtgcccgt agtgagatga                                           20

<210> SEQ ID NO 22
<211> LENGTH: 20
<212> TYPE: DNA
<213> ORGANISM: Artificial Sequence
<220> FEATURE:
<223> OTHER INFORMATION: SOX17 forward

<400> SEQUENCE: 22
cagaatccag acctgcacaa                                           20

<210> SEQ ID NO 23
<211> LENGTH: 19
<212> TYPE: DNA
<213> ORGANISM: Artificial Sequence
<220> FEATURE:
<223> OTHER INFORMATION: SOX17 reverse

<400> SEQUENCE: 23
gcggccggta cttgtagtt                                            19

<210> SEQ ID NO 24
<211> LENGTH: 22
<212> TYPE: DNA
<213> ORGANISM: Artificial Sequence
<220> FEATURE:
<223> OTHER INFORMATION: ALB forward

<400> SEQUENCE: 24
gagaccagag gttgatgtga tg                                        22

<210> SEQ ID NO 25
<211> LENGTH: 22
<212> TYPE: DNA
<213> ORGANISM: Artificial Sequence
<220> FEATURE:
<223> OTHER INFORMATION: ALB reverse

<400> SEQUENCE: 25
agttccgggg cataaaagta ag                                        22

<210> SEQ ID NO 26
<211> LENGTH: 20
<212> TYPE: DNA
<213> ORGANISM: Artificial Sequence
<220> FEATURE:
<223> OTHER INFORMATION: AAT forward

<400> SEQUENCE: 26
gaagtcaagg acaccgagga                                           20

<210> SEQ ID NO 27

-continued

```
<211> LENGTH: 20
<212> TYPE: DNA
<213> ORGANISM: Artificial Sequence
<220> FEATURE:
<223> OTHER INFORMATION: AAT reverse

<400> SEQUENCE: 27
gctggcagac cttctgtctt                                           20

<210> SEQ ID NO 28
<211> LENGTH: 20
<212> TYPE: DNA
<213> ORGANISM: Artificial Sequence
<220> FEATURE:
<223> OTHER INFORMATION: TDO2 forward

<400> SEQUENCE: 28
caaatcctct gggagttgga                                           20

<210> SEQ ID NO 29
<211> LENGTH: 20
<212> TYPE: DNA
<213> ORGANISM: Artificial Sequence
<220> FEATURE:
<223> OTHER INFORMATION: TDO2 reverse

<400> SEQUENCE: 29
gtccaaggct gtcatcgtct                                           20

<210> SEQ ID NO 30
<211> LENGTH: 20
<212> TYPE: DNA
<213> ORGANISM: Artificial Sequence
<220> FEATURE:
<223> OTHER INFORMATION: HNF4A forward

<400> SEQUENCE: 30
cgagcagatc cagttcatca                                           20

<210> SEQ ID NO 31
<211> LENGTH: 20
<212> TYPE: DNA
<213> ORGANISM: Artificial Sequence
<220> FEATURE:
<223> OTHER INFORMATION: HNF4A reverse

<400> SEQUENCE: 31
tcacacatct gtccgttgct                                           20

<210> SEQ ID NO 32
<211> LENGTH: 25
<212> TYPE: DNA
<213> ORGANISM: Artificial Sequence
<220> FEATURE:
<223> OTHER INFORMATION: G6Pase forward

<400> SEQUENCE: 32
tcaacctcgt ctttaagtgg attct                                     25

<210> SEQ ID NO 33
<211> LENGTH: 20
<212> TYPE: DNA
<213> ORGANISM: Artificial Sequence
<220> FEATURE:
<223> OTHER INFORMATION: G6Pase reverse

<400> SEQUENCE: 33
```

-continued

```
agtatacacc tgctgtgccc                                          20

<210> SEQ ID NO 34
<211> LENGTH: 20
<212> TYPE: DNA
<213> ORGANISM: Artificial Sequence
<220> FEATURE:
<223> OTHER INFORMATION: TAT forward

<400> SEQUENCE: 34
gcttcctcaa gtccaatgct                                          20

<210> SEQ ID NO 35
<211> LENGTH: 20
<212> TYPE: DNA
<213> ORGANISM: Artificial Sequence
<220> FEATURE:
<223> OTHER INFORMATION: TAT reverse

<400> SEQUENCE: 35
ctgtgatgac cactcggatg                                          20

<210> SEQ ID NO 36
<211> LENGTH: 20
<212> TYPE: DNA
<213> ORGANISM: Artificial Sequence
<220> FEATURE:
<223> OTHER INFORMATION: TTR forward

<400> SEQUENCE: 36
accggtgaat ccaagtgtcc                                          20

<210> SEQ ID NO 37
<211> LENGTH: 21
<212> TYPE: DNA
<213> ORGANISM: Artificial Sequence
<220> FEATURE:
<223> OTHER INFORMATION: TTR reverse

<400> SEQUENCE: 37
ggttttccca gaggcaaatg g                                        21

<210> SEQ ID NO 38
<211> LENGTH: 18
<212> TYPE: DNA
<213> ORGANISM: Artificial Sequence
<220> FEATURE:
<223> OTHER INFORMATION: AFP forward

<400> SEQUENCE: 38
agcttggtgg tggatgaa                                            18

<210> SEQ ID NO 39
<211> LENGTH: 20
<212> TYPE: DNA
<213> ORGANISM: Artificial Sequence
<220> FEATURE:
<223> OTHER INFORMATION: AFP reverse

<400> SEQUENCE: 39
tctgcaatga cagcctcaag                                          20
```